United States Patent
Miller et al.

(10) Patent No.: US 12,036,132 B2
(45) Date of Patent: Jul. 16, 2024

(54) EXPANDABLE SPINAL IMPLANT SYSTEM AND METHOD OF USING SAME

(71) Applicant: Warsaw Orthopedic, Inc., Warsaw, IN (US)

(72) Inventors: Keith E. Miller, Germantown, TN (US); Cristian A. Capote, Memphis, TN (US); Zain Noordin, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 18/366,101

(22) Filed: Aug. 7, 2023

(65) Prior Publication Data

US 2023/0372120 A1 Nov. 23, 2023

Related U.S. Application Data

(63) Continuation of application No. 17/246,959, filed on May 3, 2021, now Pat. No. 11,806,250, which is a
(Continued)

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30734* (2013.01); *A61F 2/30749* (2013.01); *A61F 2002/30405* (2013.01); *A61F 2002/30471* (2013.01); *A61F 2002/3052* (2013.01); *A61F 2002/30578* (2013.01); *A61F 2002/30736* (2013.01)

(58) Field of Classification Search
CPC .. A61F 2/447; A61F 2/30734; A61F 2/30749; A61F 2/4611; A61F 2002/30405; A61F 2002/3052; A61F 2002/30578; A61F 2002/30736; A61F 2002/4615
See application file for complete search history.

(56) References Cited

U.S. PATENT DOCUMENTS

| 1,677,337 A | 7/1928 | Grove |
| 3,847,154 A | 11/1974 | Nordin |

(Continued)

FOREIGN PATENT DOCUMENTS

| CN | 107 137 166 A | 9/2017 |
| DE | 44 16 605 C1 | 6/1995 |

(Continued)

OTHER PUBLICATIONS

International Search Report and Written Opinion in Application No. PCT/IB2023/057720 dated Nov. 8, 2023.
(Continued)

*Primary Examiner* — Tracy L Kamikawa
(74) *Attorney, Agent, or Firm* — FOX ROTHSCHILD LLP

(57) ABSTRACT

An expandable spinal implant is provided having first and second endplates hinged along one end and an expansion mechanism disposed therebetween configured to expand the first and second endplates from each other to provide a lordotic angle of up to 60 degrees. Various implants, systems and methods are disclosed.

14 Claims, 32 Drawing Sheets

Related U.S. Application Data continuation-in-part of application No. 16/282,654, filed on Feb. 22, 2019, now Pat. No. 11,020,239.

(60) Provisional application No. 62/633,952, filed on Feb. 22, 2018.

(56) References Cited

U.S. PATENT DOCUMENTS

| | | |
|---|---|---|
| 4,553,273 A | 11/1985 | Wu |
| 4,636,217 A | 1/1987 | Ogilvie et al. |
| 4,716,894 A | 1/1988 | Lazzeri et al. |
| 4,759,769 A | 7/1988 | Hedman et al. |
| 5,059,193 A | 10/1991 | Kuslich |
| 5,171,278 A | 12/1992 | Pisharodi |
| 5,228,811 A | 7/1993 | Potter |
| 5,284,483 A | 2/1994 | Johnson et al. |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,653,763 A | 8/1997 | Errico et al. |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,524,238 B2 | 2/2003 | Velikaris et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,635,366 B2 | 12/2009 | Abdou |
| 7,637,909 B2 | 12/2009 | Lechot et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,883,542 B2 | 2/2011 | Zipnick |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,262,710 B2 | 9/2012 | Freedman et al. |
| 8,287,597 B1 | 10/2012 | Pimenta et al. |

(56) References Cited

U.S. PATENT DOCUMENTS

| | | |
|---|---|---|
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 | 11/2013 | Prandi et al. |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 | 5/2014 | Lewis et al. |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 | 7/2015 | Matityahu |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,341 B2 | 6/2016 | Gowan |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Arnin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |

(56) References Cited

U.S. PATENT DOCUMENTS

| | | |
|---|---|---|
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |

(56) References Cited

U.S. PATENT DOCUMENTS

| | | |
|---|---|---|
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 * | 11/2020 | Weiman ............... A61F 2/442 |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |

(56) References Cited

U.S. PATENT DOCUMENTS

| | | |
|---|---|---|
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 11,285,014 B1 | 3/2022 | Josse et al. |
| 11,376,134 B1 | 7/2022 | Dewey et al. |
| 11,617,658 B2 | 4/2023 | Josse et al. |
| 11,723,780 B2 | 8/2023 | Seifert et al. |
| 2002/0045943 A1 | 4/2002 | Uk |
| 2002/0045945 A1 | 4/2002 | Liu et al. |
| 2002/0055741 A1 | 5/2002 | Schlapfer et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2002/0183762 A1 | 12/2002 | Anderson et al. |
| 2003/0050701 A1 | 3/2003 | Michelson |
| 2003/0130739 A1 | 7/2003 | Gerbec et al. |
| 2003/0163132 A1 | 8/2003 | Chin |
| 2004/0102778 A1 | 5/2004 | Huebner et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0204713 A1 | 10/2004 | Abdou |
| 2004/0249461 A1* | 12/2004 | Ferree ............... A61F 2/2846 623/17.11 |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0147478 A1 | 7/2005 | Greenberg |
| 2005/0154459 A1 | 7/2005 | Wolek et al. |
| 2005/0209698 A1 | 9/2005 | Gordon et al. |
| 2005/0228398 A1 | 10/2005 | Rathbun et al. |
| 2006/0122701 A1 | 6/2006 | Kiester |
| 2006/0129244 A1 | 6/2006 | Ensign |
| 2006/0260446 A1 | 11/2006 | Chang |
| 2006/0276901 A1 | 12/2006 | Zipnick et al. |
| 2007/0173840 A1 | 7/2007 | Huebner |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2009/0024158 A1 | 1/2009 | Viker |
| 2009/0093830 A1 | 4/2009 | Miller |
| 2009/0105834 A1 | 4/2009 | Hovda et al. |
| 2009/0292361 A1 | 11/2009 | Lopez |
| 2010/0076440 A1 | 3/2010 | Pamichev et al. |
| 2010/0082109 A1 | 4/2010 | Greenhalgh et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2011/0301577 A1 | 12/2011 | Simmen et al. |
| 2012/0004732 A1 | 1/2012 | Goel et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143195 A1 | 6/2012 | Sander |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2012/0215316 A1 | 8/2012 | Mohr et al. |
| 2013/0158664 A1 | 6/2013 | Palmatier et al. |
| 2013/0184823 A1 | 7/2013 | Malberg |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0018816 A1 | 1/2014 | Fenn et al. |
| 2014/0107790 A1 | 4/2014 | Combrowski |
| 2014/0114321 A1 | 4/2014 | Davenport et al. |
| 2014/0114420 A1 | 4/2014 | Robinson |
| 2014/0148904 A1 | 5/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0249631 A1 | 9/2014 | Weiman |
| 2014/0277471 A1 | 9/2014 | Gray et al. |
| 2014/0277473 A1 | 9/2014 | Perrow |
| 2014/0277487 A1 | 9/2014 | Davenport et al. |
| 2014/0277500 A1 | 9/2014 | Logan et al. |
| 2014/0303674 A1 | 10/2014 | Sasing |
| 2014/0364855 A1 | 12/2014 | Stoll et al. |
| 2015/0223945 A1 | 8/2015 | Weiman et al. |
| 2015/0230931 A1 | 8/2015 | Greenhalgh |
| 2015/0238236 A1 | 8/2015 | Sasing |
| 2015/0354635 A1 | 12/2015 | McClymont et al. |
| 2015/0374507 A1 | 12/2015 | Wolters et al. |
| 2016/0008924 A1 | 1/2016 | Canourgues et al. |
| 2016/0022434 A1 | 1/2016 | Robinson |
| 2016/0051373 A1 | 2/2016 | Faulhaber |
| 2016/0058571 A1 | 3/2016 | McLaughlin et al. |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0095718 A1 | 4/2016 | Burkhardt et al. |
| 2016/0199073 A1 | 7/2016 | Nino et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |

(56) References Cited

U.S. PATENT DOCUMENTS

| | | |
|---|---|---|
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0112630 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1* | 12/2017 | Predick ............... A61F 2/447 |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0271513 A1 | 9/2018 | Perrow et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0325574 A1 | 11/2018 | Bjork et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133782 A1* | 5/2019 | McLaughlin ......... A61F 2/4425 |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0329388 A1 | 10/2019 | Erickson et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0214754 A1 | 7/2020 | Bowen et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |

(56) References Cited

U.S. PATENT DOCUMENTS

| | | |
|---|---|---|
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |
| 2022/0047312 A1 | 2/2022 | Seykora et al. |
| 2022/0133336 A1 | 5/2022 | Tsai et al. |
| 2022/0133497 A1 | 5/2022 | Dewey et al. |
| 2022/0133498 A1 | 5/2022 | Josse et al. |
| 2022/0133499 A1 | 5/2022 | Josse et al. |
| 2022/0218325 A1 | 7/2022 | Josse |
| 2022/0387184 A1 | 12/2022 | Josse et al. |
| 2023/0027836 A1 | 1/2023 | Predick et al. |

FOREIGN PATENT DOCUMENTS

| | | |
|---|---|---|
| EP | 0 767 636 A1 | 4/1997 |
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102192022 B1 | 12/2020 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |
| WO | 2015063721 A1 | 5/2015 |
| WO | 2015198335 A1 | 12/2015 |
| WO | 2016057940 A1 | 4/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report, and Written Opinion for Application. No. PCT/US2019/019067, dated Jun. 3, 2019.
International Search Report, and Written Opinion for Application. No. PCT/US2019/019060, dated Jun. 5, 2019.
International Search Report and Written Opinion, PCT/IB2020/000932, Dated Jul. 29, 2021.
International Search Report and Written Opinion, PCT/IB2020/000942, Dated Aug. 10, 2021.
European Search Report, EP19756905, Dated Oct. 18, 2021.
International Search Report and Written Opinion, PCT/US2022/016809, dated Jul. 27, 2022.
International Search Report and Written Opinion in Application No. PCT/US2022/027695 dated Jul. 27, 2022.
International Search Report and Written Opinion in Application No. PCT/US2022/027200 dated Aug. 19, 2022.
International Search Report and Written Opinion in Application No. PCT/US2022/030094 dated Sep. 16, 2022.
International Search Report and Written Opinion in Application No. PCT/US2022/016831 dated Sep. 29, 2022.
Chinese Office Action in Application No. 201980010758.4 dated Jun. 16, 2023.
Chinese Office Action in Application No. 201980010758.4 dated Sep. 16, 2023.
International Search Report and Written Opinion in Application No. PCT/IB2023/058417 dated Dec. 7, 2023.

* cited by examiner

EXPANDABLE SPINAL IMPLANT SYSTEM AND METHOD OF USING SAME

CROSS-REFERENCE TO RELATED U.S. PATENT APPLICATION

This application is a continuation of U.S. application Ser. No. 17/246,959 (now U.S. Pat. No. 11,806,250), entitled "EXPANDABLE SPINAL IMPLANT SYSTEM AND METHOD OF USING SAME", filed May 3, 2021, which is a continuation in-part of U.S. application Ser. No. 16/282,654 (now U.S. Pat. No. 11,020,239), entitled "EXPANDABLE SPINAL SYSTEM AND METHOD OF USING SAME", filed Feb. 22, 2019, which claims benefit to U.S. Provisional Patent Application Ser. No. 62/633,952, entitled "EXPANDABLE SPINAL IMPLANT SYSTEM AND METHOD OF USING SAME", filed Feb. 22, 2018. The entire disclosure of each is incorporated herein by reference in its entirety.

TECHNICAL FIELD

The present disclosure generally relates to medical devices for the treatment of musculoskeletal disorders, and more particularly to a surgical system that includes an expandable spinal implant, systems for implanting an expandable spinal implant, and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody devices may be introduced to a space between adjacent vertebral bodies (the interbody space) to properly space the vertebral bodies and provide a receptacle for bone growth promoting materials.

More recently, interbody devices have been introduced that provide additional capability beyond static spacing of the vertebral bodies. For example, some devices have expansion capability such that the implant may be introduced to the interbody space in a collapsed state and then expanded to produce additional spacing and, in some cases, introduce or restore curvature to the spine by expanding selectively on only one end or portion of the implant. However, many existing expandable interbody designs have limited ranges of expansion.

An additional problem exists related to subsidence of spinal surfaces due to existing interbody devices having inadequately-sized load-bearing surfaces. In the case of expandable devices, the loads on the load-bearing surfaces, including loads generated during expansion of the implant, are often significant. An expandable implant with relatively large surface areas is needed to bear the loads, including the loads generated during implant expansion, in an attempt to avoid a need for follow-on surgery due to subsidence of spinal surfaces.

A further problem is instability of existing expandable interbody devices as they are expanded. Often, the load-bearing surfaces move relative to one another, as well as relative to an inserter, as the interbody device is expanded such that there is a risk of undesired shifts in the positioning of the interbody device within the intervertebral space.

The present invention seeks to address these and other shortcomings in the existing art.

SUMMARY

In one aspect, the present disclosure provides an expandable spinal implant deployable between a contracted position and an expanded position in a disc space between two vertebral bodies, the expandable spinal implant comprising a first endplate, the first endplate including an outer surface and an inner surface, a first endplate first end, a first endplate second end, a first endplate first lateral surface extending between the first endplate first end and the first endplate second end, an opposing first endplate second lateral surface extending between the first endplate first end and the first endplate second end; a second endplate, the second endplate including an outer surface and an inner surface, a second endplate first end, a second endplate second end, a second endplate first lateral surface extending between the second endplate first end and the second endplate second end, and an opposing second endplate second lateral surface extending between the second endplate first end and the second endplate second end, wherein the second endplate first end is pivotably engaged with the first endplate first end; an expansion mechanism disposed between the first endplate and the second endplate, the expansion mechanism including a wedge disposed between the first endplate and second endplate, the wedge including an upper surface, a lower surface, a wedge first end, a wedge second end, a wedge first lateral surface extending between the wedge first end and the wedge second end, and an opposing wedge second lateral surface extending between the wedge first end and the wedge second end, wherein the wedge comprises a wedge aperture between the wedge second end and wedge first end; a rod assembly, the rod assembly having a first end and a second end defining a longitudinal axis, wherein at least a portion of the rod assembly is disposed within the wedge aperture and operably engaged with the wedge to translate the wedge along the longitudinal axis of the rod; and wherein the wedge is operably engaged with at least one of the first endplate or second endplate and configured to expand the implant when the wedge is translated along the rod assembly in a first direction, and contract the implant when the wedge is translated along the rod assembly in a second direction.

In some embodiments, the rod assembly comprises a threaded outer surface, and the wedge aperture comprises a threaded inner surface operably engaged with the threaded outer surface of the rod.

In some embodiments, the translation of the wedge along the longitudinal axis of the rod in a first direction is towards the first and second endplate first ends. In some embodiments, translation of the wedge along the longitudinal axis of the rod in the first direction is towards the first and second endplate second ends.

In some embodiments, at least one of the first endplate or the second endplate further comprises at least one protrusion from its inner surface configured to engage a surface of the wedge. In some embodiments, at least one of the wedge first lateral surface and the wedge second lateral surface comprises a lateral post extending therefrom.

In some embodiments, at least one of the first endplate or second endplate further comprises at least one protrusion from its inner surface, wherein the at least one protrusion defines at least one lateral channel configured to receive the lateral post such that when the wedge is translated in the first direction, the lateral post of the wedge is moved in the first direction in the lateral channel to expand the implant and that when the wedge is translated in the second direction, the lateral post of the wedge is moved in the second direction in the lateral channel to contract the implant.

In some embodiments, the expandable spinal implant further comprises at least one vertebral endplate engagement component operably engaged to at least one of the first endplate or the second endplate and configured to engage with the wedge such that it protrudes from the outer surface of the first or second endplate when the wedge is translated in the first direction. In some embodiments, the vertebral endplate engagement component is configured to engage with the wedge such that it retracts from the outer surface of the first or second endplate when the wedge is translated in the second direction.

In some embodiments, the expandable spinal implant is capable of expanding up to 30 degrees, 35 degrees, 40 degrees, 45 degrees, 50 degrees, or 60 degrees or anywhere in between these amounts from 0 to 60 degrees.

In some embodiments, the expansion mechanism is secured to the second endplate. In some embodiments, the first end of the second endplate comprises a first aperture and the second end of the second endplate comprises a second aperture, and wherein the first end of the rod assembly is disposed within the first aperture and the second end of the rod assembly is disposed within the second aperture. In some embodiments, the rod assembly comprises a rod having a first and second end and a securing pin comprising a first and second end, the first end of the rod engaged with the second end of the securing pin, wherein the securing pin is disposed through the first aperture and the second end of the rod is disposed within the second aperture.

In some embodiments, the first endplate first end further comprises at least one protrusion comprising a lumen therethrough extending laterally along the first endplate first end; the second endplate first end further comprises at least one protrusion comprising a lumen therethrough extending laterally along the second endplate first end; and the lumen through the at least one protrusion on the first endplate first end is co-axially aligned with the lumen through the at least one protrusion on the second endplate first end, and a rod is disposed through the lumens to pivotably engage first endplate first end with the second endplate first end.

In some embodiments, at least one of the first or second endplate comprises an aperture disposed therethrough from the outer surface to the inner surface, the aperture configured to receive an external screw for securing the first or second endplate to a vertebral body. In some embodiments, at least one of the first or second endplate comprises a tab extending from the first or second end, wherein the tab comprises an aperture therethrough configured to receive an external screw for securing first or second endplate to a vertebral body.

In some embodiments, at least one of the outer surfaces of the first or second endplates comprise anti-migration and/or anti-expulsion features. In some embodiments, at least one of the first or second endplates comprise apertures between the inner and outer surfaces thereof to allow bone growth material to be loaded into the implant. In some embodiments, at least one of the first or second endplates is porous.

In another aspect, the present disclosure provides an expandable spinal implant system comprising an insertion instrument comprising a drive cannula and a drive shaft removably and rotatably disposed within the drive cannula, and further comprising an attachment cannula and an attachment shaft removably and rotatably disposed within the attachment cannula; and an expandable spinal implant deployable between a contracted position and an expanded position in a disc space between two vertebral bodies, the expandable spinal implant comprising a first endplate, the first endplate including an outer surface and an inner surface, a first endplate first end, a first endplate second end, a first endplate first lateral surface extending between the first endplate first end and the first endplate second end, an opposing first endplate second lateral surface extending between the first endplate first end and the first endplate second end; a second endplate, the second endplate including an outer surface and an inner surface, a second endplate first end, a second endplate second end, a second endplate first lateral surface extending between the second endplate first end and the second endplate second end, and an opposing second endplate second lateral surface extending between the second endplate first end and the second endplate second end, wherein the second endplate first end is pivotably engaged with the first endplate first end; an expansion mechanism disposed between the first endplate and the second endplate, the expansion mechanism including a wedge disposed between the first endplate and second endplate, the wedge including an upper surface, a lower surface, a wedge first end, a wedge second end, a wedge first lateral surface extending between the wedge first end and the wedge second end, and an opposing wedge second lateral surface extending between the wedge first end and the wedge second end, wherein the wedge comprises a wedge aperture between the wedge second end and wedge first end; a rod assembly, the rod assembly having a first end and a second end defining a longitudinal axis, wherein at least a portion of the rod assembly is disposed within the wedge aperture and operably engaged with the wedge to translate the wedge along the longitudinal axis of the rod; and wherein the wedge is operably engaged with at least one of the first endplate or second endplate and configured to expand the implant when the wedge is translated along the rod assembly in a first direction, and contract the implant when the wedge is translated along the rod assembly in a second direction.

In another aspect, the present disclosure provides a method of deploying an expandable spinal implant in a disc space between two vertebral bodies, the method comprising utilizing an expandable spinal implant deployable between a contracted position and an expanded position in a disc space between upper and lower vertebral bodies, the expandable spinal implant comprising a first endplate, the first endplate including an outer surface and an inner surface, a first endplate first end, a first endplate second end, a first endplate first lateral surface extending between the first endplate first end and the first endplate second end, an opposing first endplate second lateral surface extending between the first endplate first end and the first endplate second end; a second endplate, the second endplate including an outer surface and an inner surface, a second endplate first end, a second endplate second end, a second endplate first lateral surface extending between the second endplate first end and the second endplate second end, and an opposing second endplate second lateral surface extending between the second endplate first end and the second endplate second end, wherein the second endplate first end is pivotably engaged with the first endplate first end; an expansion mechanism disposed between the first endplate and the second endplate, the expansion mechanism including a wedge disposed between the first endplate and second endplate, the wedge including an upper surface, a lower surface, a wedge first end, a wedge second end, a wedge first lateral surface extending between the wedge first end and the wedge second end, and an opposing wedge second lateral surface extending between the wedge first end and the wedge second end, wherein the wedge comprises a wedge aperture between the wedge second end and wedge first end; a rod assembly, the rod assembly having a first end and a second end defining a longitudinal axis, wherein at least a portion of the rod assembly is disposed within the wedge aperture and operably engaged with the wedge to translate the wedge along the longitudinal axis of the rod; and wherein the wedge is operably engaged with at least one of the first endplate or second endplate and configured to expand the implant when the wedge is translated along the rod assembly in a first direction, and contract the implant when the wedge is translated along the rod assembly in a second direction; inserting the implant in the collapsed position into the disc space between the upper and lower vertebral bodies; and expanding the first and second endplates.

In other aspects of the present disclosure, various other implants, systems and methods are disclosed.

BRIEF DESCRIPTION OF THE DRAWINGS

The present disclosure is further informed by the specific description accompanied by the following drawings, in which.

Figure 1:
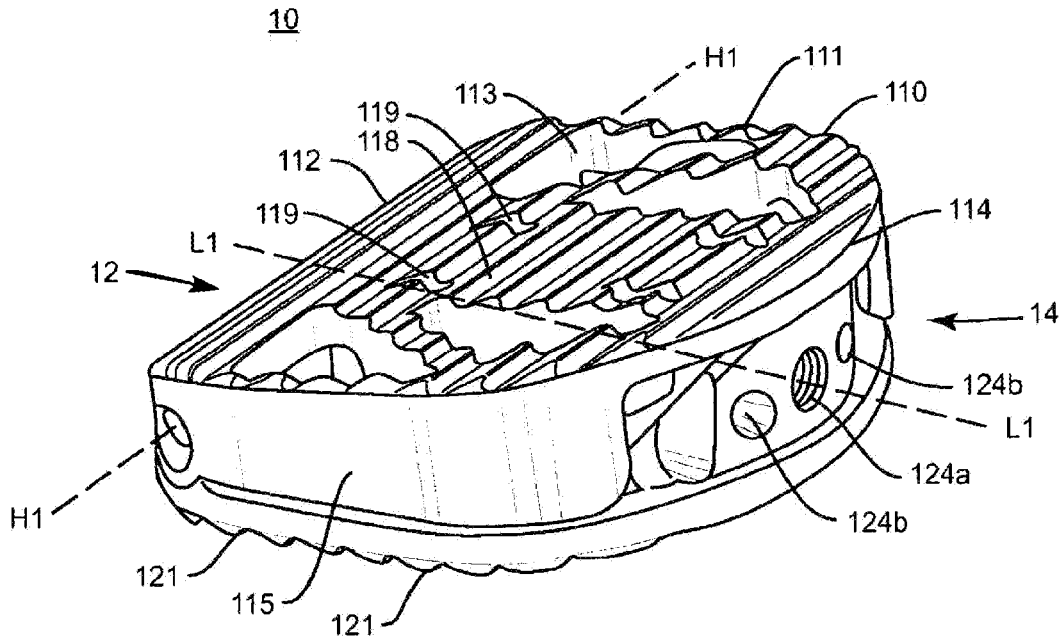
FIG. 1 is a perspective view of one embodiment of an expandable spinal implant in a closed configuration in accordance with the principles of the present disclosure.

Common numbering schemes in FIGS. 1-39 (e.g., 1xx, 2xx and 3xx), indicate similar components of implants 10, 20, and 30.

DETAILED DESCRIPTION

The exemplary embodiments of the surgical system and related methods of use disclosed are discussed in terms of medical devices for the treatment of musculoskeletal disorders and more particularly, in terms of an expandable surgical implant system that may include an expandable spinal implant, an insertion instrument, specialized instruments such as, for example, an expandable retractor and a spinal surgical table that rotates and bends the patient in various directions, and/or a method or methods for treating a spine.

In some embodiments, the present system includes an expandable spinal implant suitable for insertion from an oblique, postero-lateral procedures and/or transforaminal lumbar interbody fusions (sometimes referred to as TLIF procedures), direct posterior (sometimes referred to as PLIF procedures), direct lateral (sometimes referred to as DLIF procedures), anterior lumbar interbody fusions (sometimes referred to as ALIF procedures), or variations of these procedures, in which the present implant is inserted into an intervertebral space and then expanded in order to impart and/or augment a lordotic and/or kyphotic curve of the spine.

In some embodiments, the spinal implant system may also be employed to restore and/or impart sagittal balance to a patient by increasing and/or restoring an appropriate lordotic and/or kyphotic angle between vertebral bodies at a selected level where the spinal implant is implanted and expanded. In the various embodiments described, the spinal implant system may be useful in a variety of complex spinal procedures for treating spinal conditions beyond one-level fusions. Furthermore, the spinal implant system described in the enclosed embodiments may also be used as a fusion device with an expandable height for tailoring the implant to a particular interbody disc space to restore the spacing between adjacent vertebral bodies and facilitate spinal fusion between the adjacent vertebral bodies.

In some embodiments, and as mentioned above, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components, e.g., a "first end" of an end plate and a "first end" of a wedge, indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise. The term "bone growth promoting material" as used herein may include, but is not limited to: bone graft (autograft, allograft, xenograft) in a variety of forms and compositions (including but not limited to morselized bone graft); osteoinductive material such as bone morphogenetic proteins (BMP) (including but not limited to INFUSE® available from Medtronic) and alternative small molecule osteoinductive substances; osteoconductive materials such as demineralized bone matrix (DBM) in a variety of forms and compositions (putty, chips, bagged (including but not limited to the GRAFTON® family of products available from Medtronic)); collagen sponge; bone putty; ceramic-based void fillers; ceramic powders; and/or other substances suitable for inducing, conducting or facilitating bone growth and/or bony fusion of existing bony structures. Such bone growth promoting materials may be provided in a variety of solids, putties, liquids, colloids, solutions, or other preparations suitable for being packed or placed into or around the various implant 10, 20, 30 embodiments described herein.

The following discussion includes a description of a surgical system including one or more spinal implants, related components and methods of employing the surgical system in accordance with the principles of the present disclosure. Various alternate embodiments are disclosed and individual components of each embodiment may be used with other embodiments. Reference is made in detail to the exemplary embodiments of the present disclosure, which are illustrated in the accompanying figures. Turning to FIGS. 1-36, there are illustrated components of a surgical system, such as, for example, an expandable spinal implant 10, 20, and 30.

The components of the expandable spinal implant systems described herein can be fabricated from biologically acceptable materials suitable for medical applications, including metals, synthetic polymers, ceramics and bone material and/or their composites. For example, the components of expandable spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaprolactone and their combinations.

Various components of spinal implant system may be formed or constructed of material composites, including but not limited to the above-described materials, to achieve various desired characteristics such as strength, rigidity, elasticity, compliance, biomechanical performance, durability and radiolucency or imaging preference. The components of expandable spinal implant system, individually or collectively, may also be fabricated from a heterogeneous material such as a combination of two or more of the above-described materials. The components of the expandable spinal implant systems may be monolithically formed, integrally connected or include fastening elements and/or instruments, as described herein. For example, in some embodiments the expandable spinal implant systems may comprise expandable spinal implants 10, 20, 30 comprising PEEK and/or titanium structures with radiolucent markers (such as tantalum pins and/or spikes) selectively placed in the implant to provide a medical practitioner with placement and/or sizing information when the expandable spinal implant 10, 20, 30 is placed in the spine. The components of the expandable spinal implant system may be formed using a variety of subtractive and additive manufacturing techniques, including, but not limited to machining, milling, extruding, molding, 3D-printing, sintering, coating, vapor deposition, and laser/beam melting. Furthermore, various components of the expandable spinal implant system may be coated or treated with a variety of additives or coatings to improve biocompatibility, bone growth promotion or other features. For example, the endplates 110, 120, 210, 220, 310, 320 may be selectively coated with bone growth promoting or bone ongrowth promoting surface treatments that may include, but are not limited to: titanium coatings (solid, porous or textured), hydroxyapatite coatings, or titanium plates (solid, porous or textured).

The expandable spinal implant system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the expandable spinal implant system may be employed with surgical procedures, as described herein, and/or, for example, corpectomy, discectomy, fusion and/or fixation treatments that employ spinal implants to restore the mechanical support function of vertebrae. In some embodiments, the expandable spinal implant system may be employed with surgical approaches, including but not limited to: anterior lumbar interbody fusions (ALIF), posterior lumbar interbody fusion (PLIF), oblique lumbar interbody fusion, transforaminal lumbar interbody fusion (TLIF), various types of anterior fusion procedures, and any fusion procedure in any portion of the spinal column (sacral, lumbar, thoracic, and cervical, for example).

Generally in FIGS. 1-36, three exemplary embodiments of an expandable spinal implant 10, 20, and 30 are shown (implant 10 is highlighted in exemplary FIGS. 1-13, implant 20 is highlighted in exemplary FIGS. 14-26, and implant 30 is highlighted in exemplary FIGS. 27-36). Expandable spinal implants 10, 20, and 30 may comprise first and second endplates operably engaged via a hinge mechanism that lordotically or angularly expands the endplates relative to one another via a wedge mechanism driven perpendicularly to the axis of the hinge joint. In some embodiments, the wedge drive direction may be oriented at an oblique angle between 0 and 90 degrees to the hinge axis. In some embodiments, the first and second endplates may lordotically expand when the wedge mechanism is driven towards the hinge. In other embodiments, the first and second endplates may lordotically expand when the wedge mechanism is driven away from the hinge.

As shown in FIGS. 1-13, an expandable spinal implant 10 is configured to be inserted in an intervertebral disc space between adjacent vertebral bodies. The implant 10 includes a first end 12 and a second end 14 defining a mid-longitudinal axis L1-L1 therebetween. In some embodiments, the expandable spinal implant 10 comprises a first endplate 110 and second endplate 120. First endplate 110 includes a first end 112, a second end 114, two opposing side surfaces 115 extending from the first end 112 of the first endplate to a portion of the second end 114 of the first endplate, and with the first endplate being therebetween, an inner surface 116, and an outer surface 118. Second endplate 120 includes a first end 122, a second end 124, two opposing side surfaces 125 extending from the first end 122 of the second endplate to a portion of the second end 124 of the second endplate, and with the second endplate being therebetween, an inner surface 126, and an outer surface 128. In one embodiment, endplates 110, 120 include projections 111, 121 configured to engage a surface of an endplate of an adjacent vertebral body (not shown). Projections 111, 121 may comprise various anti-migration, anti-expulsion, and/or osseointegration features including, but not limited to: ridges, teeth, pores, and coatings (including but not limited to porous titanium coatings such as those provided on Capstone PTC™ implants available from Medtronic). The endplates 110, 120 may further comprise at least one opening 113, 123 defined therein, configured to allow bone growth materials to be packed, placed, or loaded into implant 10.

Figure 7:
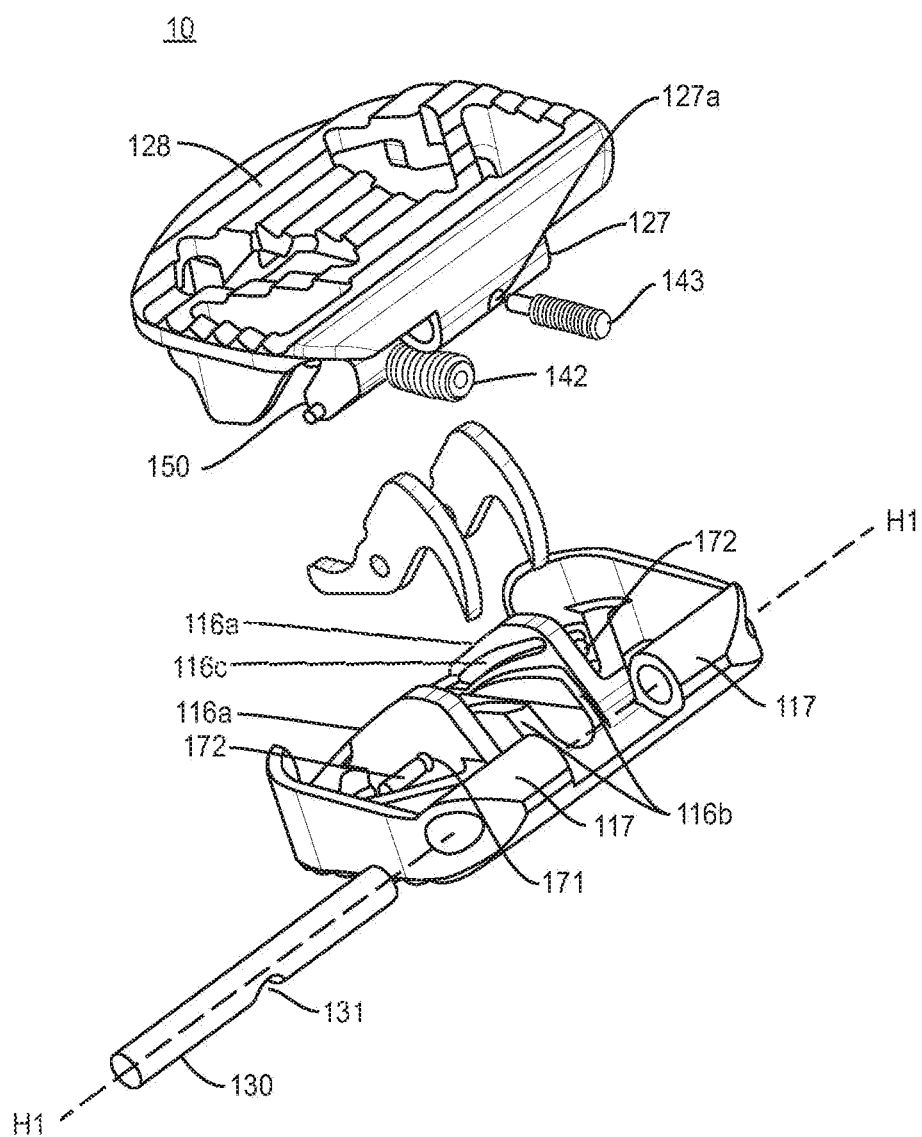
FIG. 7 is an exploded perspective view of one embodiment of an expandable spinal implant in an expanded configuration in accordance with the principles of the present disclosure.
Figure 8:
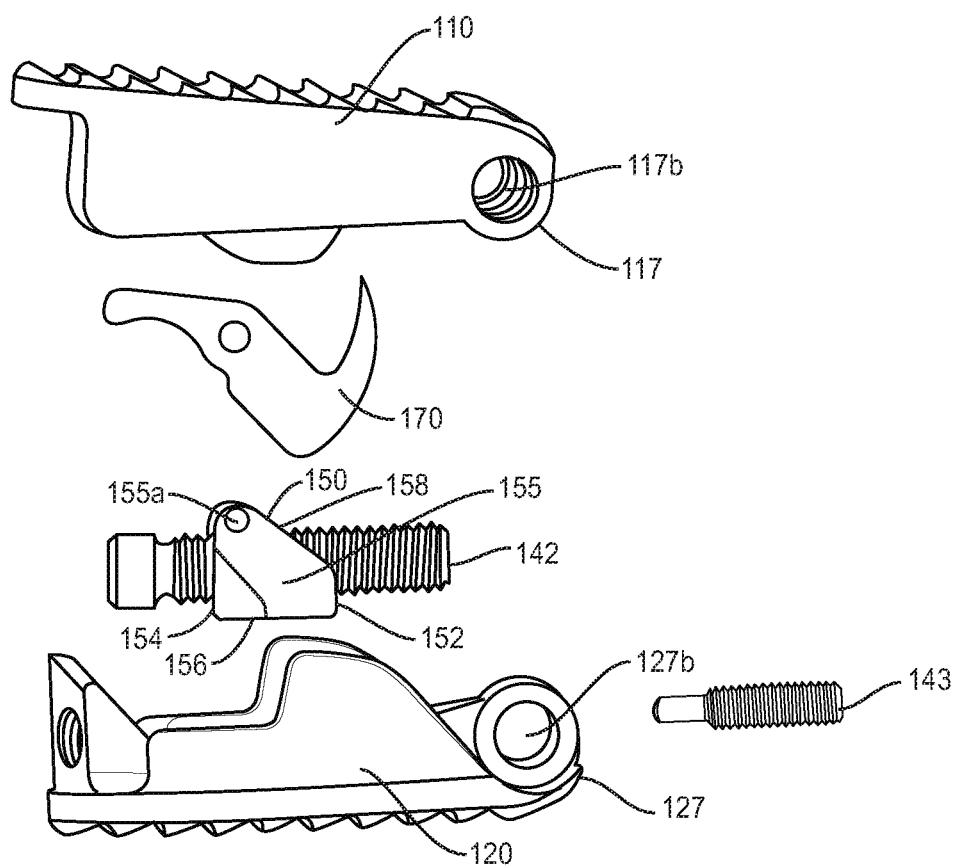
FIG. 8 is an exploded side view of one embodiment of an expandable spinal implant in an expanded configuration in accordance with the principles of the present disclosure.
Figure 9:
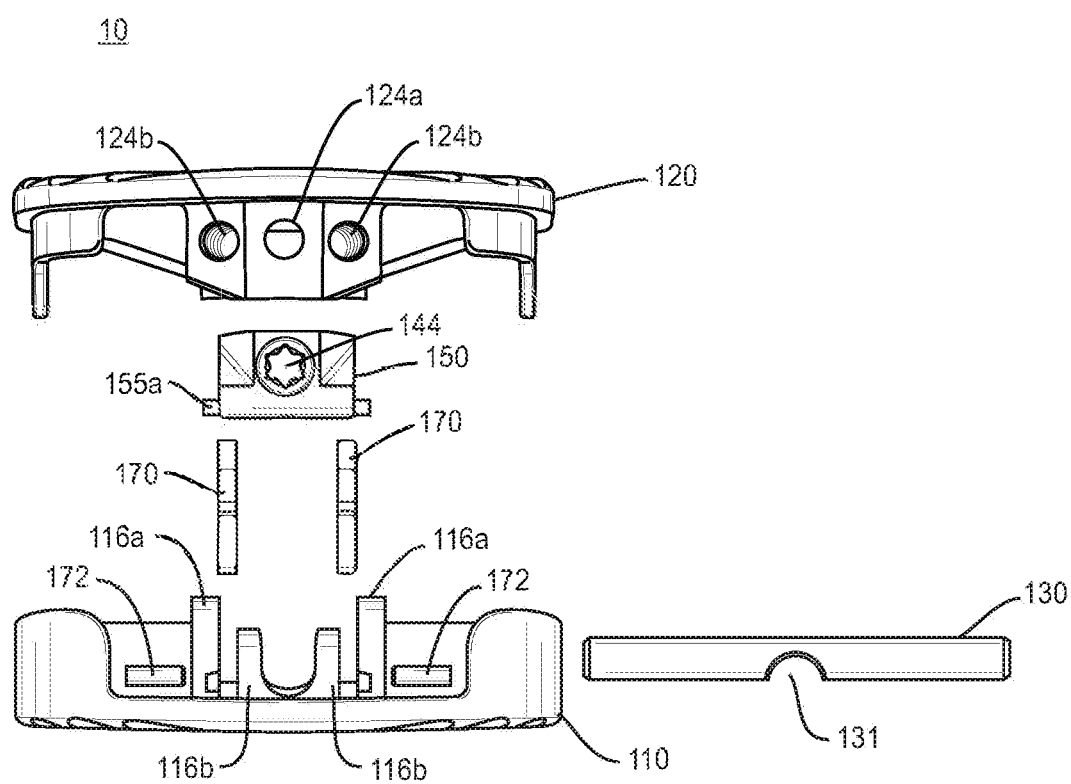
FIG. 9 is an exploded end view of one embodiment of an expandable spinal implant in an expanded configuration in accordance with the principles of the present disclosure.
Figure 10:
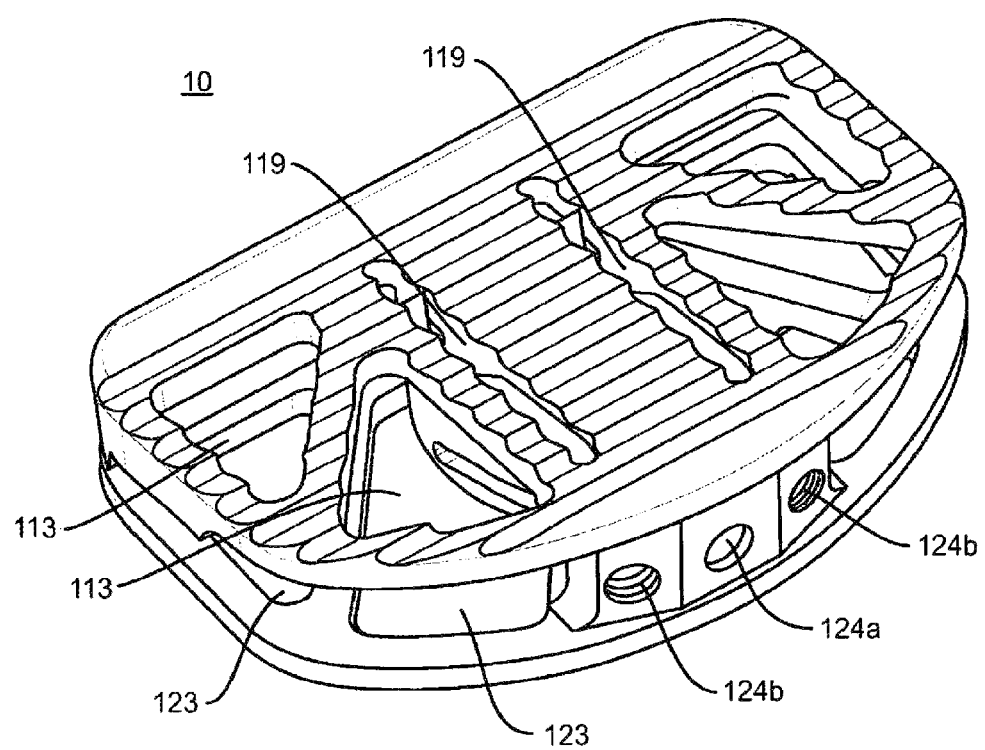
FIG. 10 is a perspective view of one embodiment of an expandable spinal implant in a closed configuration in accordance with the principles of the present disclosure.
Figure 11:
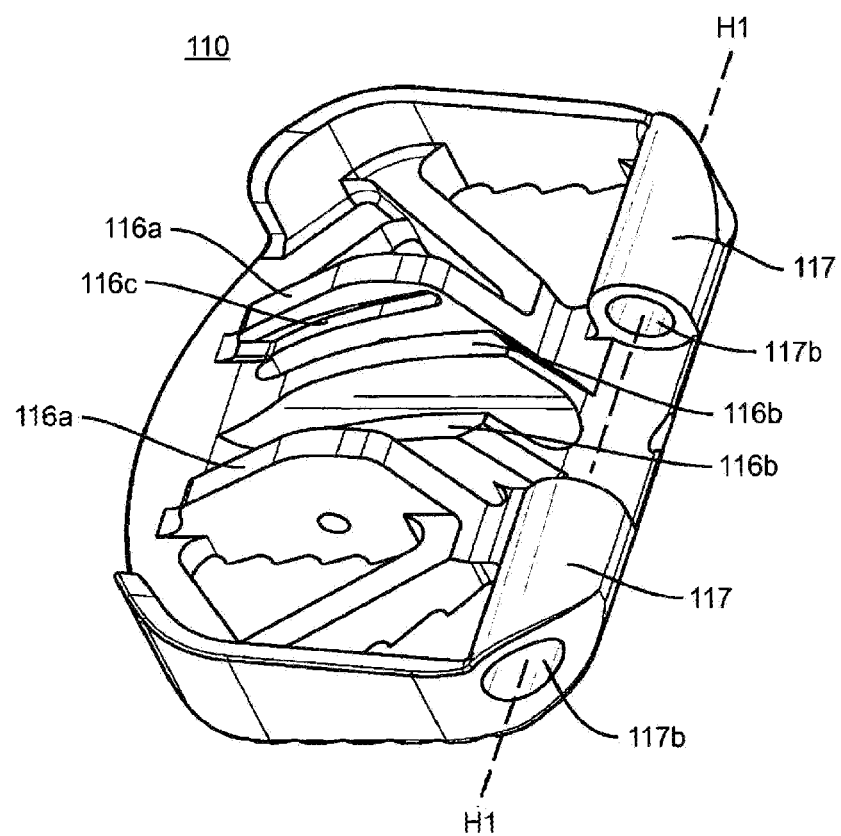
FIG. 11 is a perspective view of the inner surface of one embodiment of an endplate in accordance with the principles of the present disclosure.
Figure 12:
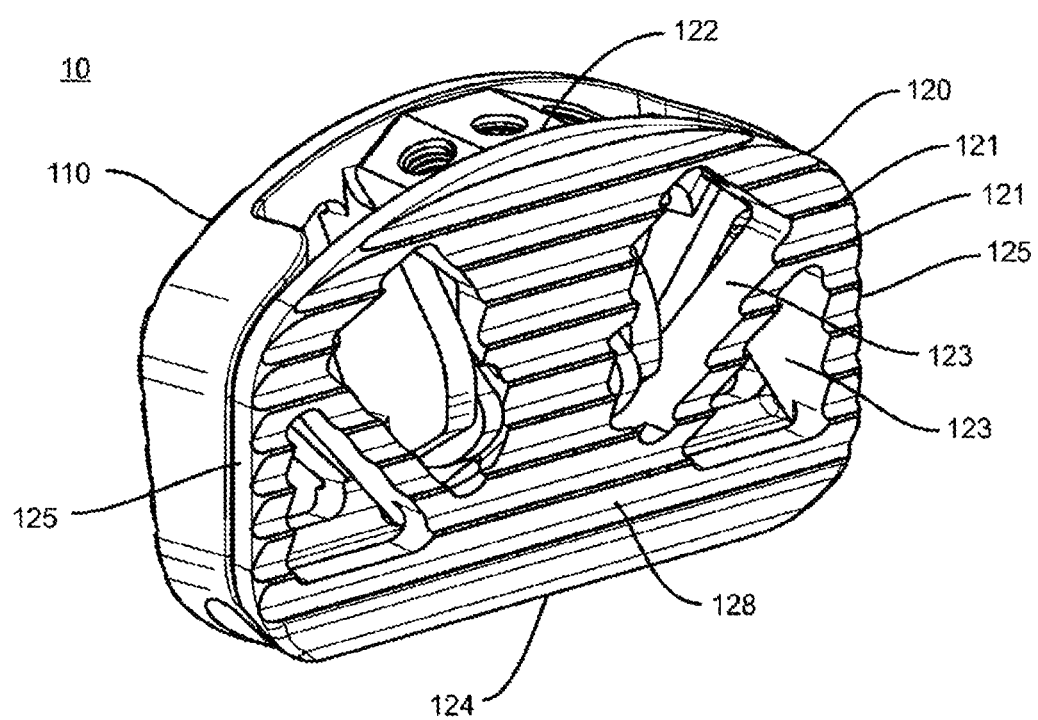
FIG. 12 is a perspective view of the outer surface of one embodiment of an endplate in accordance with the principles of the present disclosure.

Referring generally to FIGS. 1-12, endplates 110, 120 may be operably engaged via a hinge mechanism located near or on first ends 112 and 122. For example, as shown in FIG. 7, first end 112 of first endplate 110 may comprise first and second hinge protrusions 117 extending along at least a portion of the length of first end 112 perpendicular to mid-longitudinal axis L1-L1. In some embodiments, first and second hinge protrusions are cylindrical and extend from lateral side surfaces 115 towards the mid-longitudinal axis L1-L1, and further comprise lumen 117b extending therethrough. First end 122 of second endplate 120 may also comprise a hinge protrusion 127. In some embodiments, hinge protrusion 127 is cylindrical and extends laterally along first end 122, and further comprises a lumen 127b extending therethrough. The lumen of first and second hinge protrusions 117 and lumen of hinge protrusion 127 may be co-axially aligned along a hinge axis H1-H1. A pin 130 may be disposed within the lumen of hinge protrusions 117, 127 to pivotably engage first endplate 110 to second endplate 120. In this way, first endplate 110 may hinge and/or rotate away from second endplate 120 such that the distance between second ends 114 and 124 is increased along radial arc R. While a simple pin and lumen hinge is shown in some of the pictured embodiments, it should be understood that other types of hinge and/or connection mechanisms may also be used to operably engage the endplates 110, 120 of the implant. For example, in some embodiments, a "living hinge" may be utilized wherein the endplates 110, 120 are at least partially integrally formed at the hinge point but with cut-outs or flex points that allow the endplates 110, 120 to rotate about the hinge connection. Endplates 110, 120 may be operably engaged in a number of different ways including but not limited to: integral connections, separable connections, mechanically fixed connections using fastener or adhesives, releasable connections (including, but not limited to keyways and partially open hinges), and other connection types. In some embodiments, endplates 110, 120 may be integrally formed using additive manufacturing techniques such as 3D printing, sintering laser/beam melting, casting, extruding, or machined in an integral form using subtractive manufacturing techniques from one or more stock materials.

As described herein, the implant 10 may include an expansion mechanism for expanding endplates 110, 120 to increase the lordotic angle R of implant 10. In some embodiments, the expansion mechanism of implant 10 includes a rod assembly 140 having a longitudinal axis E3-E3 comprising a rod 142, a securing pin 143 and wedge 150 mounted within the implant between first endplate 110 and second endplate 120. Wedge 150 may comprise a first end 152, a second end 154, an upper surface 158, a lower surface 156, and opposing lateral surfaces 155 extending between the first and second ends. Wedge 150 may further comprise an aperture 151 between the first and second ends. Rod assembly 140 may comprise rod 142 disposed within aperture 151. In some embodiments, rod 142 comprises a threaded outer surface 141 configured to be engaged with a complimentary inner threaded surface of aperture 151 of wedge 150 such that the wedge 150 travels forward and backwards along rod 142 between first and second ends of implant 10 when rod 142 is rotated relative to wedge 150. In some embodiments, rod 142 and securing pin 143 may be integrally formed, and in such embodiments, it will be understood that integral rod assembly 140 may be interchanged with rod 142 in the discussions below.

The expansion mechanism of implant 10 may be operably engaged with first or second endplates 110, 120. In some embodiments, the expansion mechanism of implant 10 is secured to second endplate 120. Hinge protrusion 127 of second endplate 120 may comprise a first end aperture 127a through the walls of hinge protrusion 127 and generally perpendicular to lumen 127b therethrough. Second end 124 of second endplate 120 may further comprise an aperture 124a therethrough. In some embodiments, apertures 127a and 124a are generally co-axial. One or both ends of rod assembly 140 may be secured within one or both of aperture 124a of second end 124 and first aperture 127a of hinge protrusion 127 along first end 122 to operably engage the expansion mechanism of implant 10 with second endplate 120. In the embodiment shown, second end of rod 142 is secured within aperture 124a, and a cylindrical securing pin 143 disposed through aperture 127a coaxially engages an end of rod 142 to further secure the expansion mechanism within implant 10. Pin 130 disposed within the lumen of hinge protrusions 117, 127 may include a cut out portion 131 to allow rod 142 and/or cylindrical securing pin 143 to be disposed through aperture 127a. In some embodiments, rod assembly 140 is disposed such that longitudinal axis E1-E1 is substantially parallel to mid-longitudinal axis L1-L1 of implant 10 (i.e., perpendicular to hinge axis H1-H1). In some embodiments, apertures 124a and 127a may be aligned such that rod assembly 140 is disposed such that longitudinal axis E1-E1 is at an oblique angle to the mid-longitudinal axis L1-L1 of implant 10 (e.g., between zero and 90 degrees).

Rod 142 may be rotatable within apertures 124a, 127a relative to implant 10. Inner surface 116 of first endplate 110 may comprise guidewalls 116a extending away from the inner surface 116 of first endplate 110. In some embodiments, guidewalls 116a extend perpendicularly away from inner surface 116 of first endplate 110. In some embodiments, guidewalls 116a are oriented substantially parallel to the longitudinal axis L of rod 142 and are disposed a width W apart from one another. In some embodiments, the width W is substantially similar to the width of wedge 150, with wedge 150 being disposed between guidewalls 116a. Lateral sides 155 of wedge 150 engage with guidewalls 116a such that rotation of wedge 150 relative to implant 10 is prevented. In this way, the interaction between threaded surfaces 141, 151 cause wedge 150 to translate along longitudinal axis L of rod 142 when rod 142 is rotated.

Wedge 150 may include an upper surface 158 configured to engage with inner surface 116 of first endplate 110 and lordotically expand first endplate 110 away from second endplate 120 when wedge 150 is moved towards first end 12 of implant 10. For example, upper surface 158 may be ramped or wedge-shaped and suitable for urging a complementary ramped or contoured surface on the inside of first endplate 110 so as to gradually move first endplate 140 away from second endplate 150 as wedge 150 is advanced towards first end 12 along rod 142. In the embodiment depicted, inner surface 116 of first endplate 110 may further comprise ramps 116b to engage upper surface 158 of wedge 150. In some embodiments, the expansion mechanism may be configured such that lower surface 156 of wedge 150 engages inner surface 126 of second endplate 120 alternatively to, or in addition to, upper surface 158 engaging inner surface 116 of first endplate 110. In some embodiment, the expansion mechanism may be configured to lordotically expand implant 10 when wedge 150 is moved towards the second end 14 of implant 10.

In some embodiments, the ramp mechanism 158/116b may cooperate with one or more paired lateral posts 155a and channel 116c system in order to optimize the opening and/or expansion of implant 10. Guidewalls 116a may comprise lateral channels 116c. Channels 116c may be angled or partially angled to provide a mechanism for assisting in the expansion of implant 10 as wedge 150 is advanced along rod 142 towards the hinge at first end 12 of implant 10. Wedge 150 may comprise one or more lateral posts 155a that engage with channels 116c to provide an expansion mechanism configured to urge first endplate 110 away from second endplate 120 when wedge 150 is moved towards first end 12 of implant 10. Post 155a and channel 116c mechanism may also aid in making expansion of the implant 10 substantially reversible such that when wedge 150 is moved away from the hinge, lateral posts 155a are moved in a second direction in the lateral channels 116c to contract first endplate 110 towards second endplate 120 (which may result in implant 10 returning to the closed or unexpanded configuration shown generally in FIG. 1). This reversible feature, combined with the threaded interaction between rod 142 and wedge 150, renders implant 10 capable of being incrementally expanded or contracted through a substantially infinite adjustable range of motion (bounded only by the length of the channels 116c). The length and orientation of channels 116c may be adjusted to determine the amount of lordotic expansion. In some embodiments, the design of the expansion mechanism, including the length and orientation of channels 116c, is configured to allow up to 30 degrees, 35 degrees, 40 degrees, 45 degrees, 50 degrees, or 60 degrees or anywhere in between these amounts from 0 to 60 degrees or more of lordotic expansion as wedge 150 is moved towards the hinge assembly.

In some embodiments, various designs may be used to optimize the interaction of wedge 150 with first endplate 110. Such configurations may include, but are not limited to: sequential ramps or tapered surfaces with varying angles; shallow angle sequential ramps or tapered surfaces leading into higher angle sequential ramps or tapered surfaces, as well as other opening mechanisms (such as the lateral post 155a and channel 116c system described above that may combine to assist the ramps in expanding implant 10).

As described above, the expansion mechanism 140, 150 of implant 10 is secured to second endplate 120 such that first endplate 110 is urged away from expansion mechanism 140, 150 and second endplate 120 when wedge 150 is moved towards first end 12 of implant 10. In some embodiments, only a first end 145 of rod assembly 140 may be secured to first and/or second endplates 110, 120 such that the a second end 146 of rod assembly 140 may move relative to endplates 110, 120 as implant 10 is expanded or contracted. In such embodiments, lower surface 156 of wedge 150 may be ramped or wedge-shaped and suitable for urging a complementary ramped or contoured surface on the inside of second endplate 120 so as to gradually move the endplates 110, 120 away from each other as the wedge 150 is advanced along the rod 142. Inner surface 126 of second endplate 120 comprise ramps to engage lower surface 156 of wedge 150, and/or may comprise guidewalls with channels disposed therein to engage lateral posts extending from wedge 150, similar to those described above for the interaction of upper surface 158 of wedge 150 with inner surface 116 of first endplate 110. In some embodiments, various designs may be used to optimize the interaction of wedge 150 with endplates 110, 120. Such configurations may include, but are not limited to: sequential ramps or tapered surfaces with varying angles; shallow angle sequential ramps or tapered surfaces leading into higher angle sequential ramps or tapered surfaces, as well as other opening mechanisms (such as the lateral post 155a and channel 116c system described above that may combine to assist the ramps in expanding the implant 10).

As wedge 150 moves towards the hinge, the mechanism loses mechanical advantage because the lever arm between the wedge and hinge joint decreases during expansion. This provides increased force feedback to a medical practitioner using implant 10, giving the medical practitioner a better feel of anatomical constraints. To supplement the expansion force, implant 10 may be specifically paired or used with other surgical instruments that manipulate the spine. These surgical instruments include, for example, surgical tables, patient positioning frames, and the like, that manipulate the patient and may for example further facilitate and/or adjust access to one or more disc spaces by bending the spine of a patient in various directions and adjusting the orientation of the patient to ease or facilitate access to the spinal surgical location(s). Exemplary surgical tables, patient positioning frames, and the like, and related methods of using them include those described in, e.g., U.S. patent application Ser. Nos. 15/239,239, 15/239,256, 15/337,157, 15/638,802, 15/639,080, 15/672,005, and 15/674,456, all incorporated herein by reference in their entirety.

In some embodiments, second end 146 of rod 142 may comprise an interface 144 configured to be operably engaged by a drive shaft (not shown) to rotate rod 142. Rod interface 144 may comprise a drive receptacle configured to cooperate with an implant-engaging end of the drive shaft. The drive connection between the driver shaft and rod interface 144 may comprise a variety of drive interfaces including but not limited to: multi-lobular drives; hexalobular drives; cross or Phillips head drives; straight or "flat head" drives; square or other polygonal drives; and/or combinations thereof. In other embodiments, first end 145 of rod assembly 140 (via rod 142 or securing pin 143) may further comprise an interface configured to be operably engaged by a drive shaft to rotate rod assembly 140. In this way, implants of the present disclosure may be expanded from both an anterior/oblique and posterior approach.

Figure 2:
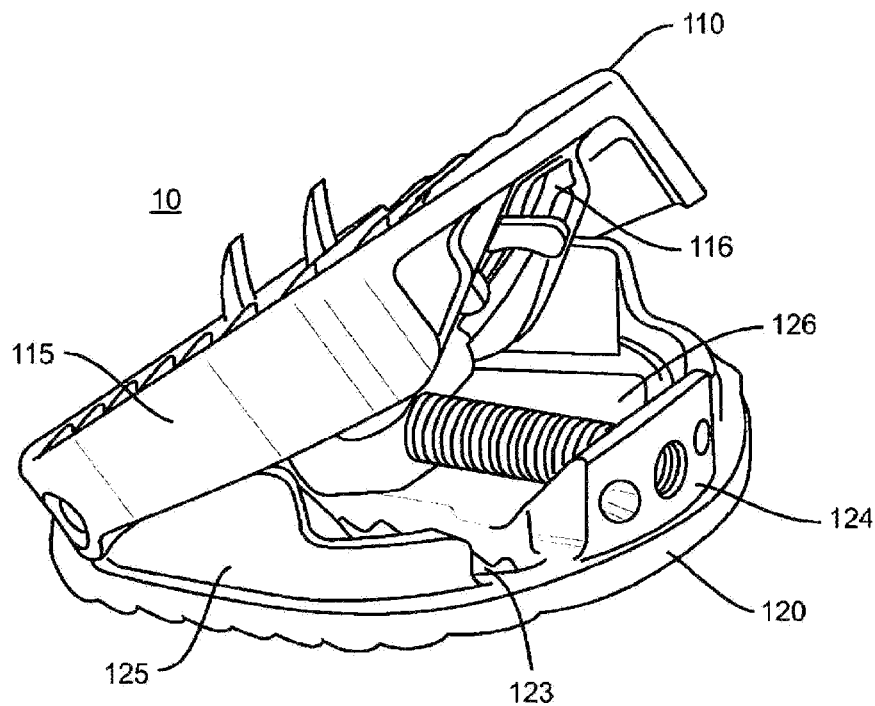
FIG. 2 is a perspective view of one embodiment of an expandable spinal implant in an expanded configuration in accordance with the principles of the present disclosure.
Figure 3:
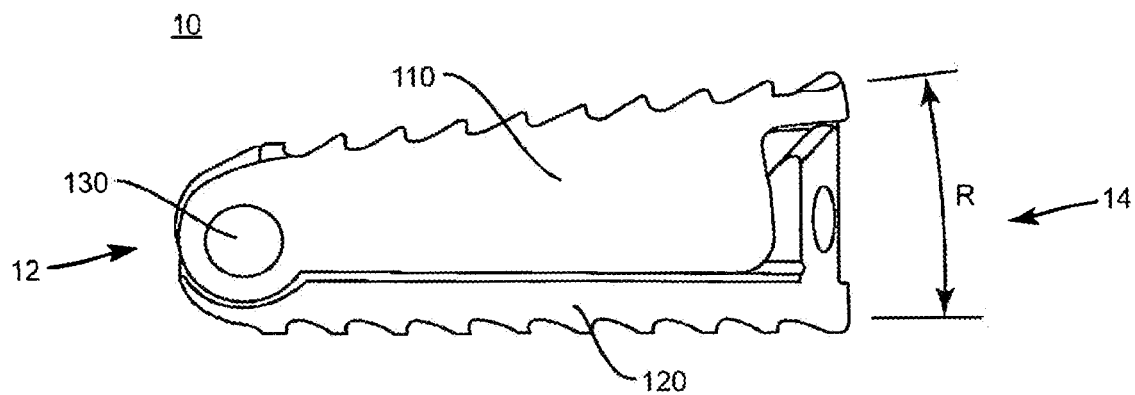
FIG. 3 is a side view of one embodiment of an expandable spinal implant in a closed configuration in accordance with the principles of the present disclosure.
Figure 4:
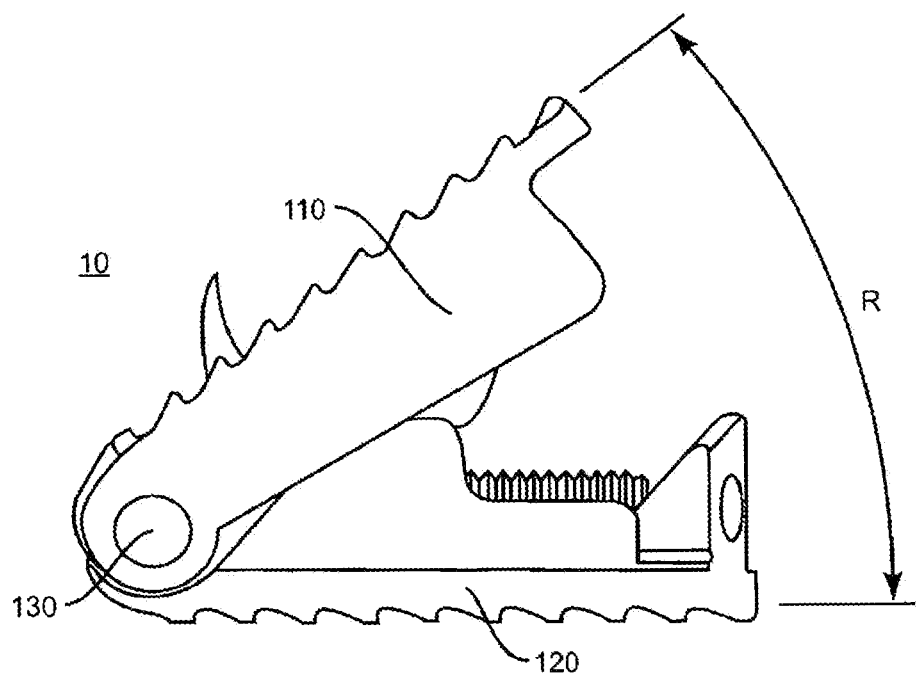
FIG. 4 is a side view of one embodiment of an expandable spinal implant in an expanded configuration in accordance with the principles of the present disclosure.
Figure 5:
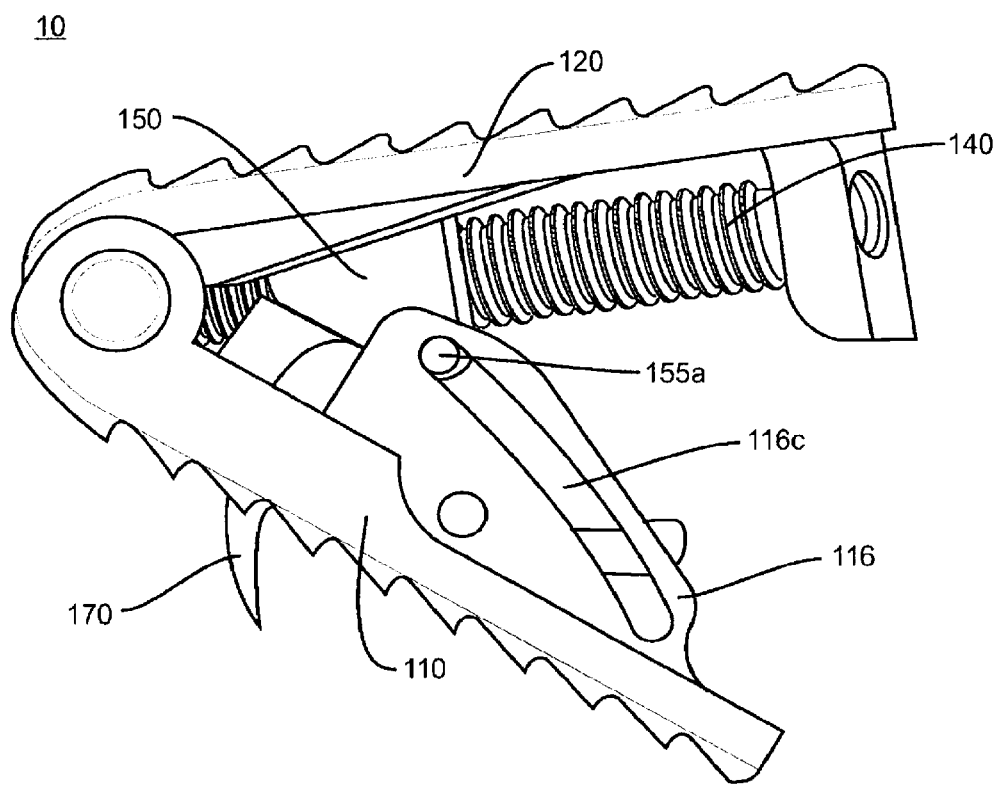
FIG. 5 is a side view of one embodiment of an expandable spinal implant in an expanded configuration in accordance with the principles of the present disclosure.
Figure 6:
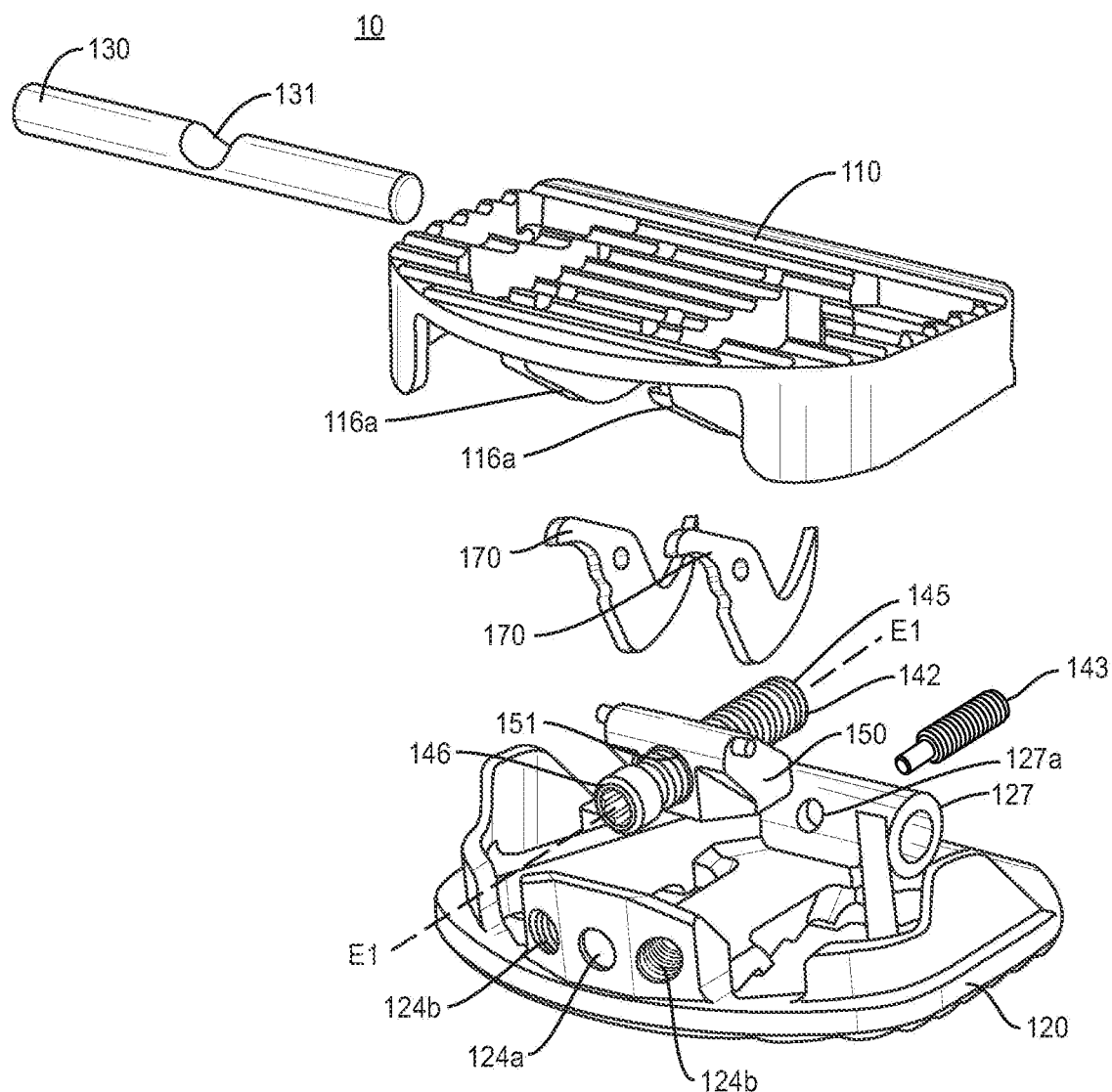
FIG. 6 is an exploded perspective view of one embodiment of an expandable spinal implant in an expanded configuration in accordance with the principles of the present disclosure.

In some embodiments, implant 10 may further comprise vertebral endplate engagement components 170 which are configured to engage the vertebral endplate as the implant 10 is expanding. In some embodiments, vertebral endplate engagement components 170 may be claw- or hook-shaped. It is contemplated that vertebral endplate engagement components 170 may comprise various configurations suitable to engage the vertebral endplate to decrease or prevent potential migration or expulsion of the device from the intervertebral space. As shown in FIGS. 1 and 3, when implant 10 is in a collapsed, closed, or unexpanded state, vertebral endplate engagement components 170 may be retracted within the device to allow for easy insertion into the disc space. As shown in FIGS. 2 and 4, as implant 10 is expanded, and vertebral endplate engagement components 170 protrude from implant 10 and engage the vertebral endplate to decrease potential migration of the device. In the embodiment depicted in FIGS. 1-12, the vertebral endplate engagement components 170 are mounted between guidewalls 116a and disposed adjacent upper surface 158 of wedge 150. Guidewalls 116a may each comprise an aperture 171 through which a pin 172 is disposed to mount vertebral endplate engagement components 170 to first endplate 110. In some embodiments, vertebral endplate engagement components 170 are at least partially rotatable about pin 172. Vertebral endplate engagement components 170 may be shaped to engage upper surface 158 of wedge 150 as wedge 150 is moved towards first end 12 of implant 10, causing the teeth 170 to partially rotate about pin 172 and protrude through apertures 119 of first endplate 110 and engage the vertebral endplate. As wedge 150 is moved away from first end 12, a separate portion of vertebral endplate engagement components 170 may engage upper surface 158 of wedge 150 to retract vertebral endplate engagement components 170 back into the interior of implant 10. In an alternative embodiment (not shown), vertebral endplate engagement components 170 could be incorporated into a piston. Wedge 150 would engage the piston as implant 10 is expanded. In another embodiment (not shown), vertebral endplate engagement components 170 could be mounted onto a rotating gear. A mating gear on wedge 150 would engage the rotating gear and rotate vertebral endplate engagement components 170 into engagement with the vertebral endplate as the wedge 150 expands implant 10. In another embodiment (not shown), rod assembly 140 may engage vertebral endplate engagement components 170 directly, via, e.g., threaded outer surface 141.

Although FIGS. 1-12 depict vertebral endplate engagement components 170 protruding only from first endplate 110, other embodiments may include vertebral endplate engagement components protruding from second endplate 120, or from both endplates 110, 120. In some embodiments, implant 10 may be secured through intrinsic screws placed through apertures between inner and outer surfaces of endplates 110 or 120 (as depicted for implant 20 in FIGS. 18, 19 and discussed below). These screws may be further held in place by external locking mechanisms such as washers, springs, plates or covers that cover or push against at least a portion of the screw top or head. In other embodiments the screws may be held in place by interference fit in the screw hole and/or by features in the screw hole adding friction fit and/or holding force to the screw top or head. In other embodiments, implant 10 may be secured through integrated tabs on endplates 110 or 120 (as depicted for implant 30 in FIG. 30 and as discussed below) or separable plates that may cover a portion of the intervertebral implant.

Figure 13:
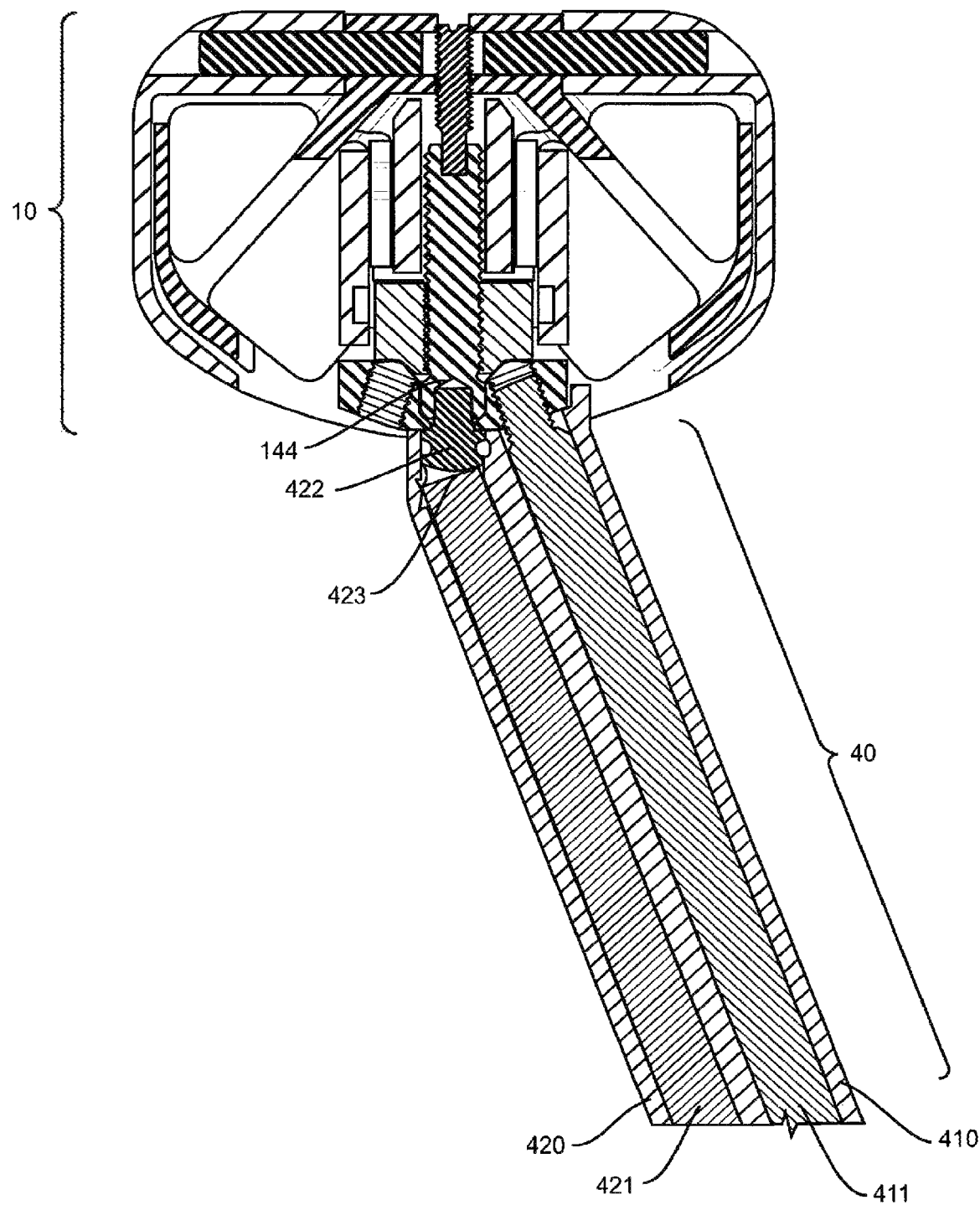
FIG. 13 is a top cutaway view of one embodiment of an expandable spinal implant and inserter in accordance with the principles of the present disclosure.
Figure 14:
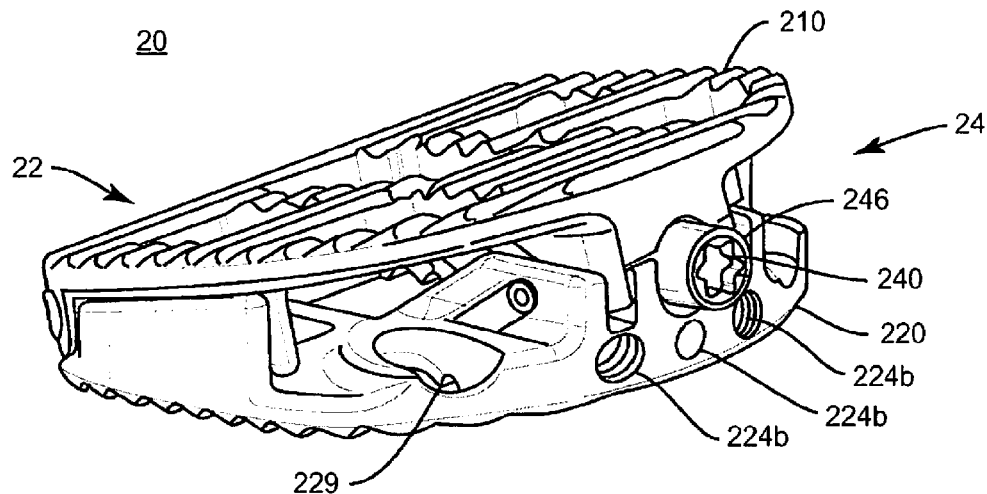
FIG. 14 is a perspective view of one embodiment of an expandable spinal implant in a closed configuration in accordance with the principles of the present disclosure.
Figure 15:
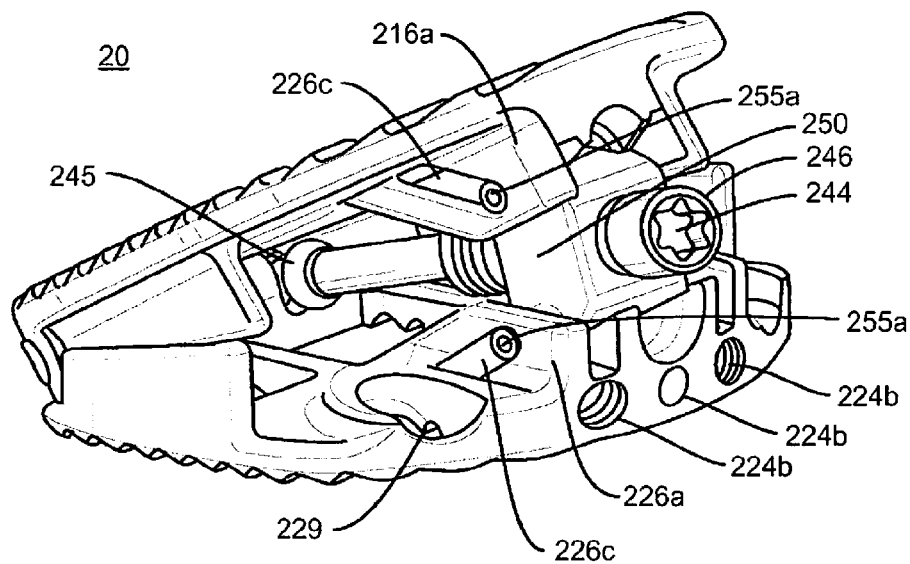
FIG. 15 is a perspective view of one embodiment of an expandable spinal implant in an expanded configuration in accordance with the principles of the present disclosure.
Figure 16:
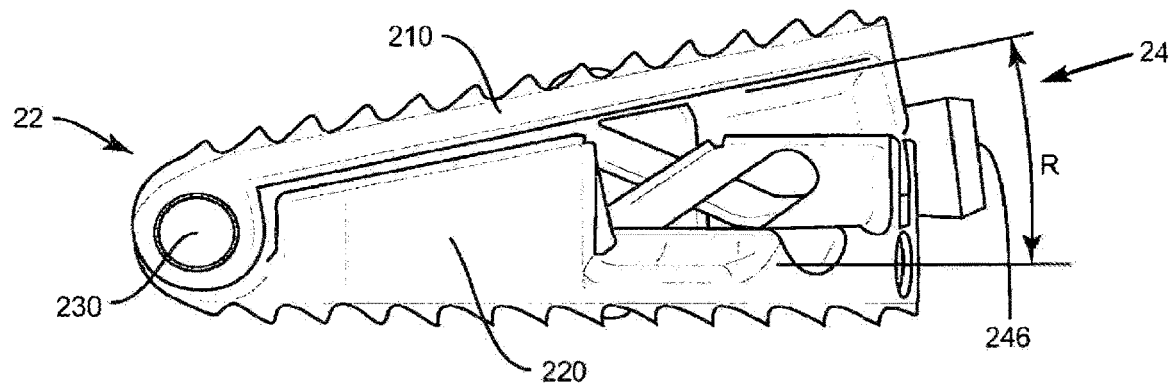
FIG. 16 is a side view of one embodiment of an expandable spinal implant in a closed configuration in accordance with the principles of the present disclosure.
Figure 17:
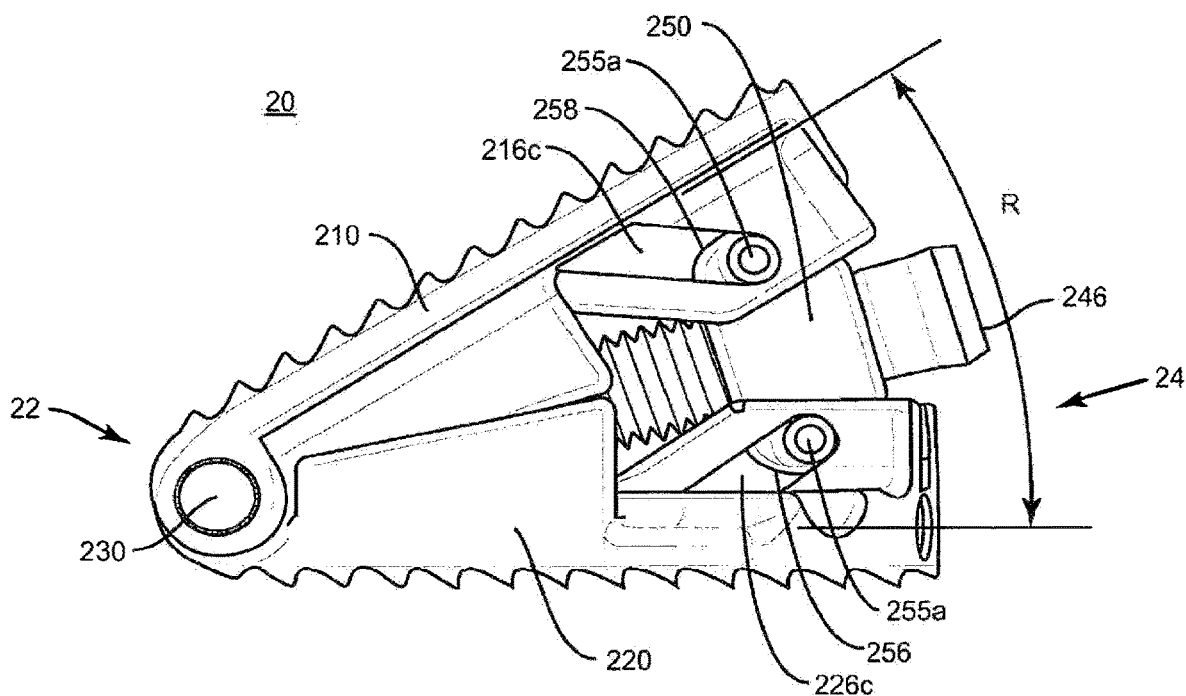
FIG. 17 is a side view of one embodiment of an expandable spinal implant in an expanded configuration in accordance with the principles of the present disclosure.
Figure 18:
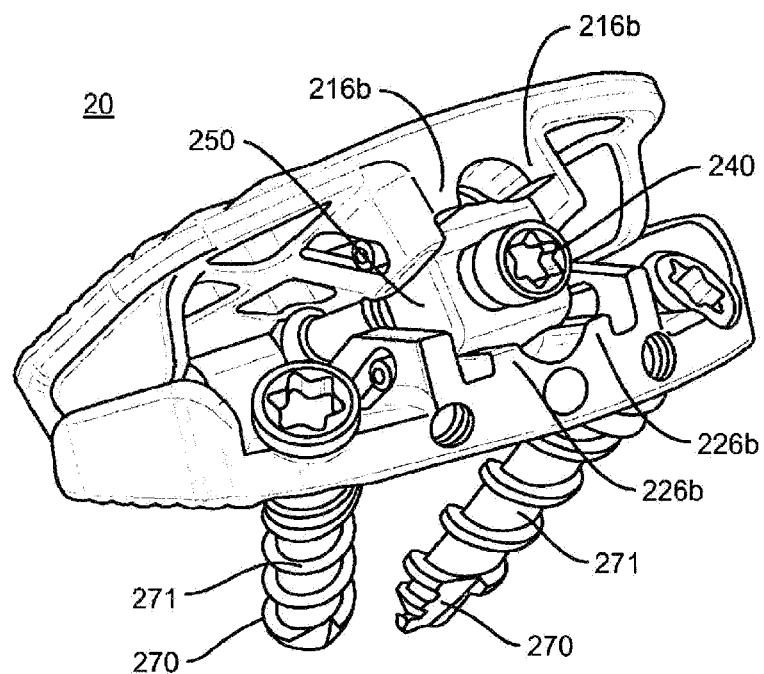
FIG. 18 is a perspective view of one embodiment of an expandable spinal implant in an expanded configuration in accordance with the principles of the present disclosure.
Figure 19:
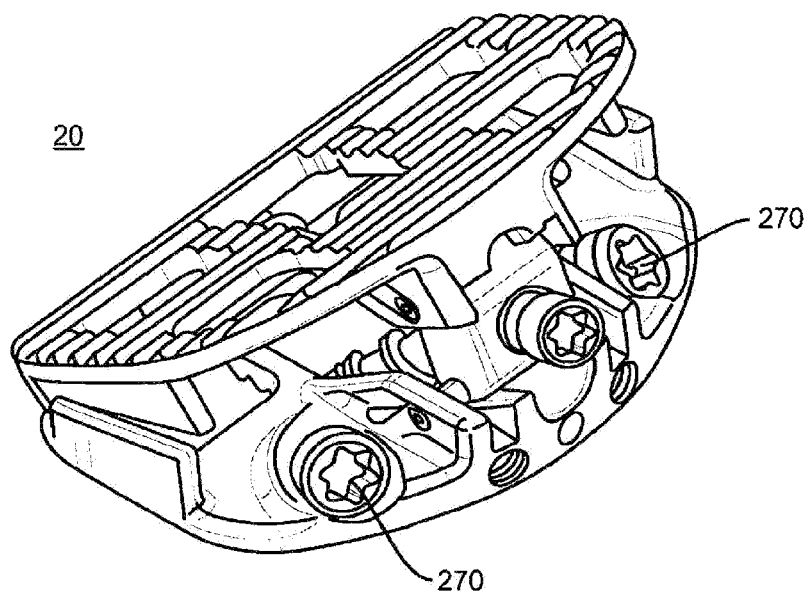
FIG. 19 is a perspective view of one embodiment of an expandable spinal implant in an expanded configuration in accordance with the principles of the present disclosure.
Figure 20A:
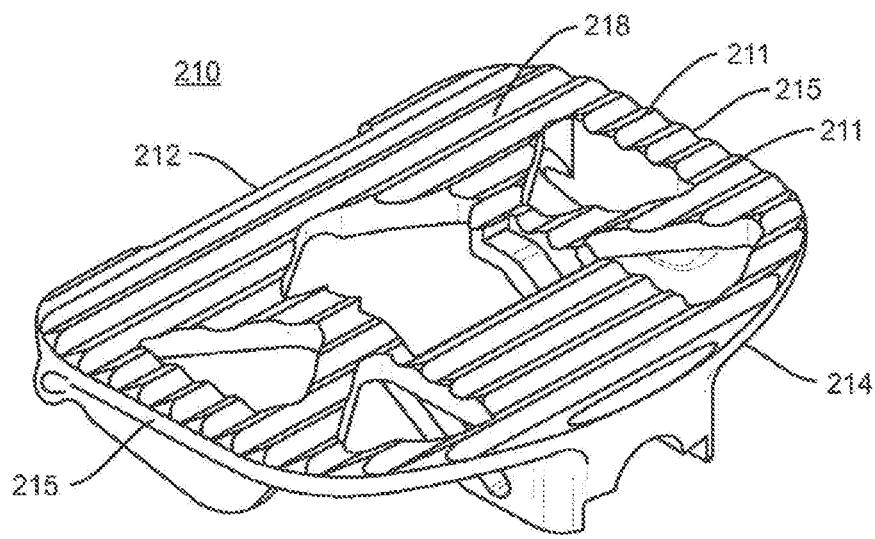
FIG. 20A is a perspective view and FIG. 20B is a plane view of the outer surface of one embodiment of an endplate in accordance with the principles of the present disclosure.
Figure 20B:
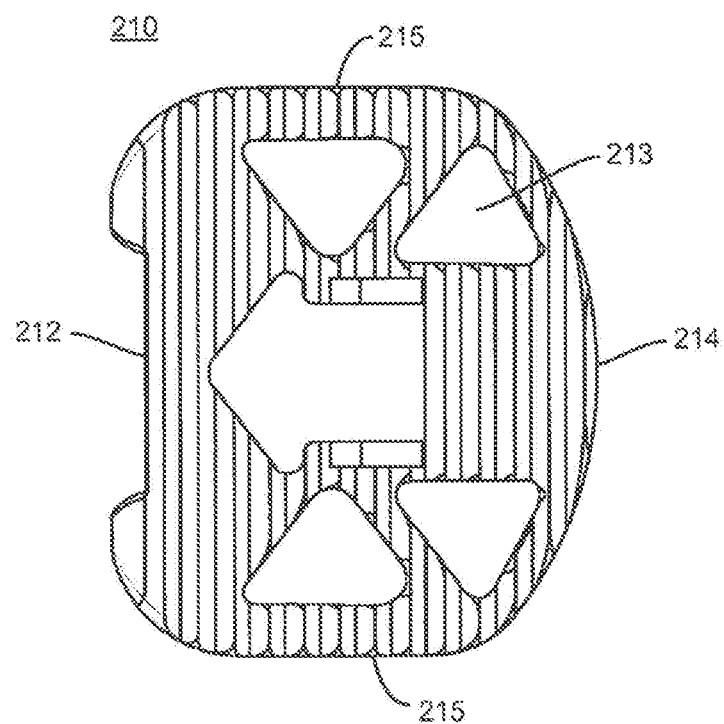

FIG. 13 shows an implant 10 in use with an insertion instrument 40 to form an expandable spinal implant system according to one embodiment. As shown generally in FIG. 13, the system may comprise an insertion instrument 40 comprising an attachment cannula 410 and a driver cannula 420. Insertion instrument 40 may further comprise an attachment shaft 411 removably and rotatably disposed within attachment cannula 410 and a drive shaft 421 removably and rotatably disposed within driver cannula 420. The implant engaging end of attachment shaft 411 may comprise a threaded outer surface. Insertion instrument 40 may further comprise a drive engagement component 422 connected to the end of drive shaft 421 via, for example, a u-joint 423.

The system may also further comprise an expandable spinal implant 10 configured to be operably engaged with the insertion instrument 40 using a variety of mechanisms. As described herein, second end 14 of implant 10 may be configured to receive the tool end of insertion instrument 40 to manipulate expandable implant 10. In one embodiment, second end 124 of second endplate 120 of implant 10 comprises attachment apertures 124b disposed laterally adjacent to aperture 124a. These apertures 124b may be spaced and angled relative to mid-longitudinal axis L1-L1 of implant 10 as desired for particular surgical techniques. In some embodiments, apertures 124b may be parallel to mid-longitudinal axis L1-L1 of implant 10. In the depicted embodiment, the axis of apertures 124b is angled at approximately 15 degrees relative to mid-longitudinal axis L1-L1. Apertures 124b may comprise an inner threaded surface for engaging the threaded outer surface on the implant engaging end of attachment shaft 411. In other embodiments, the implant engaging end of attachment shaft 411 may interact with tabs or slots defined by one or both of endplates 110, 120. The attachment shaft 411 may be coaxially placed within the attachment cannula 410 and rotatable therein using the manual end of the attachment cannula (not shown). The manual end of the attachment shaft 411 may comprise a keyed or faceted surface configured for engagement with a quick-release handle (not shown) or a powered driver (not shown) for rotating attachment shaft 411.

In some embodiments, as shown in FIG. 13, interface 144 of rod 142 may be configured to be operably engaged by an implant engaging end of drive shaft 421 to translate (by threaded rotation, for example) wedge 150 along rod 142. Drive shaft 421 may be coaxially placed within drive cannula 420 and rotatable therein using the manual end of drive shaft 421 (not shown). The manual end of drive shaft 421 may comprise a keyed or faceted surface configured for engagement with a quick-release handle (not shown) or a powered driver (not shown) for rotating the drive shaft 421. Furthermore, rod interface 144 may comprise a drive receptacle configured to cooperate with an implant engaging end of drive shaft 421. The drive connection between drive shaft 421 and rod interface 144 may comprise a variety of drive interfaces including but not limited to: multi-lobular drives; hexalobular drives; cross or Phillips head drives; straight or "flat head" drives; square or other polygonal drives; and/or combinations thereof. In some embodiments, drive shaft 421 engages rod interface 144 via a drive engagement component 422 connected to the end of drive shaft 421 via, for example, a u-joint 423. U-joint 423 allows for angulation between the drive shaft 421 and rod assembly 140.

FIGS. 14-26 show various configurations of an implant 20 embodiment according to the present disclosure. Implant 20 is generally similar in construction to implant 10 described above and implant 30 described below, and comprises a first endplate 210 and second endplate 220 operably engaged to one another via a hinge mechanism along an implant first end 22, and an expansion mechanism comprising a rod assembly 240 and a wedge 250 disposed therebetween. First endplate 210 includes a first end 212, a second end 214, opposing side surfaces 215 extending from the first end 212 of the first endplate to a portion of the second end 214 of the first endplate, and with the first endplate being therebetween, an inner surface 216, and an outer surface 218. Second endplate 220 includes a first end 222, a second end 224, two opposing side surfaces 225 extending from the first end 222 of the second endplate to a portion of the second end 224 of the second endplate, and with the second endplate being therebetween, an inner surface 226, and an outer surface 228. In one embodiment, the endplates 210, 220 includes projections 211, 221 configured to engage a surface of the endplate of the adjacent vertebral body (not shown). Projections 211, 221 may comprise various anti-migration, anti-expulsion, and/or osseointegration features including, but not limited to: ridges, teeth, pores, and coatings (including but not limited to porous titanium coatings such as those provided on Capstone PTC™ implants available from Medtronic). Endplates 210, 220 may further comprise at least one opening 213, 223 defined therein, configured to allow bone growth materials to be packed, placed, or loaded into implant 20.

The endplates 210, 220 may be operably engaged via a hinge mechanism located near or on the first ends 212 and 222. For example, first end 212 of first endplate 210 may comprise first and second hinge protrusions 217 extending along at least a portion of the length of first end 212 perpendicular to mid-longitudinal axis L2-L2. In some embodiments, first and second hinge protrusions are cylindrical and extend from lateral side surfaces 215 towards the mid-longitudinal axis L2-L2, and further comprise lumen 217b extending therethrough. First end 222 of second endplate 220 may also comprise a hinge protrusion 227. In some embodiments, hinge protrusion 227 is cylindrical and extends laterally along first end 122, and further comprises a lumen 227b extending therethrough. Lumens 217b, 227b of hinge protrusions 217, 227 may be co-axially aligned along a hinge axis H2-H2. A pin 230 may be disposed within lumens 217b, 227b of hinge protrusions 217, 227 to pivotably engage first endplate 210 to second endplate 220.

Figure 25:
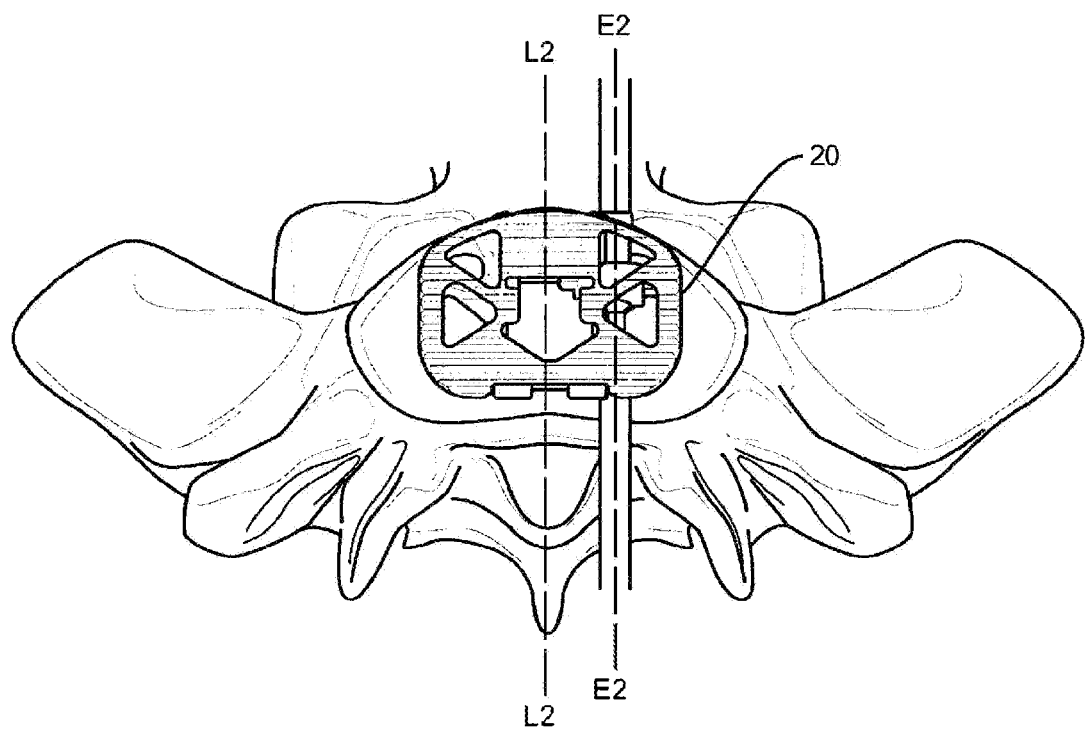
FIG. 25 is a top view of one embodiment of an expandable spinal implant as used in a spinal procedure in accordance with the principles of the present disclosure.
Figure 26:
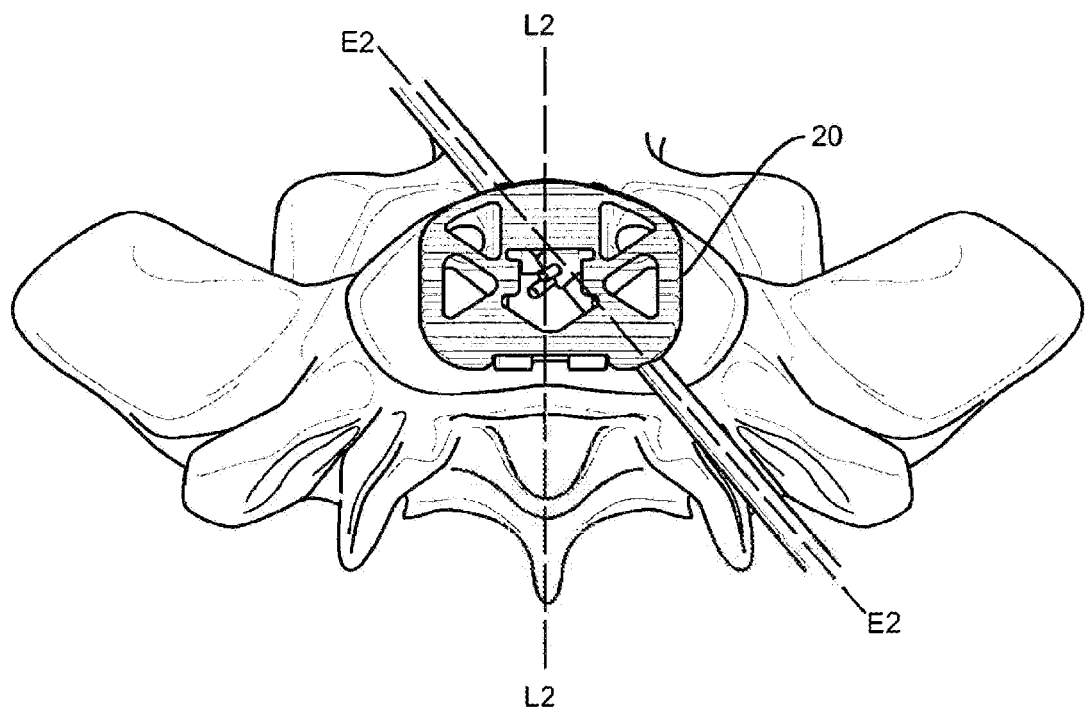
FIG. 26 is a top view of one embodiment of an expandable spinal implant as used in a spinal procedure in accordance with the principles of the present disclosure.
Figure 27:
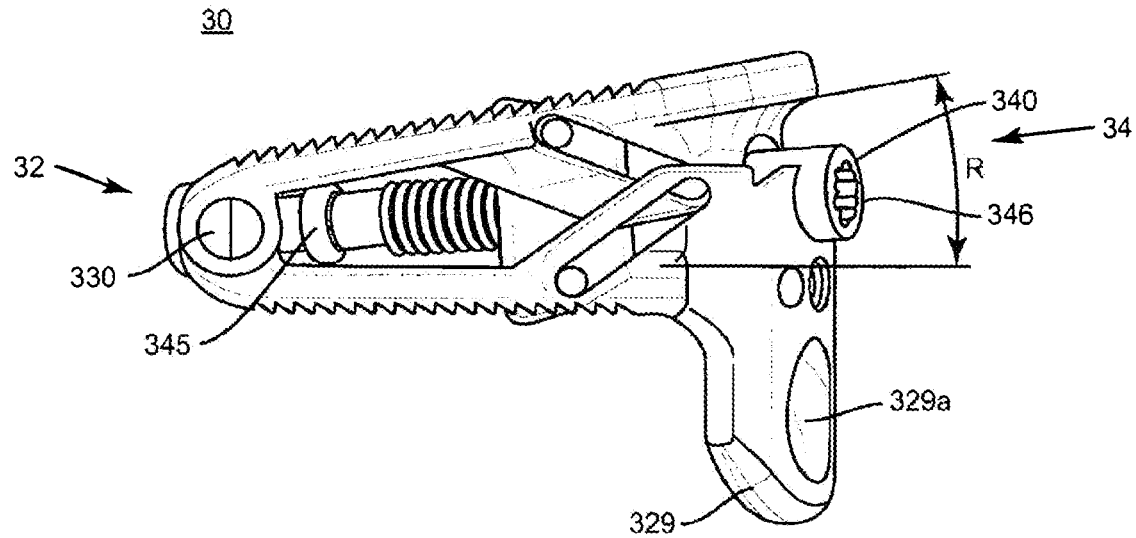
FIG. 27 is a side view of one embodiment of an expandable spinal implant in a closed configuration in accordance with the principles of the present disclosure.
Figure 28:
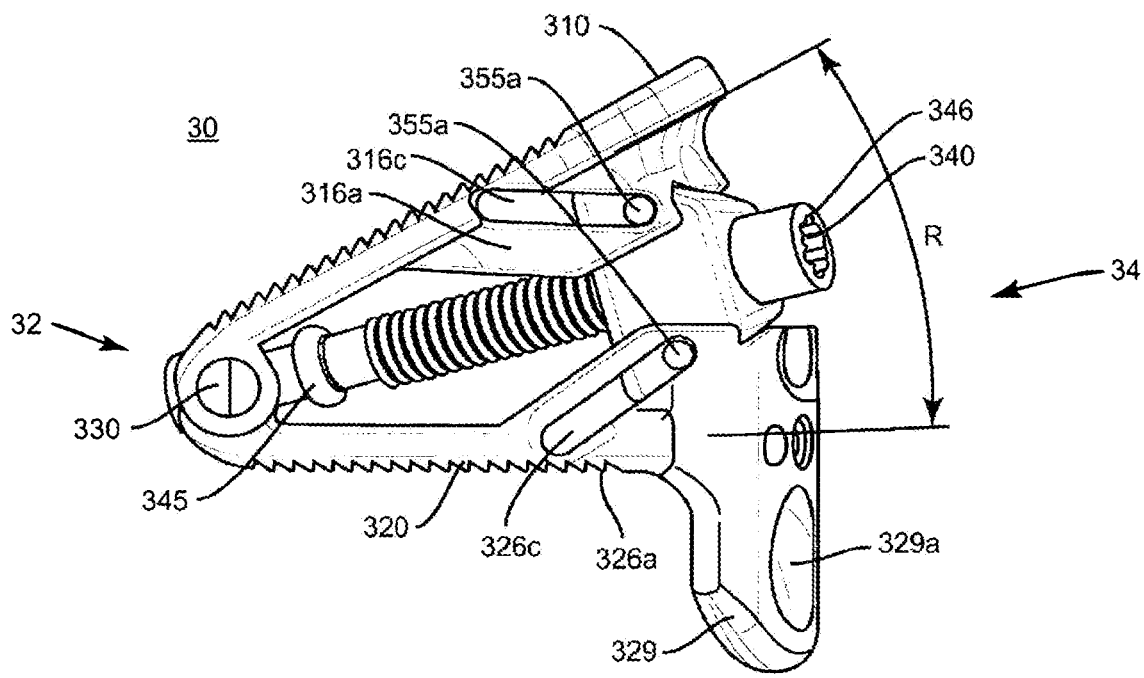
FIG. 28 is a side view of one embodiment of an expandable spinal implant in an expanded configuration in accordance with the principles of the present disclosure.
Figure 29:
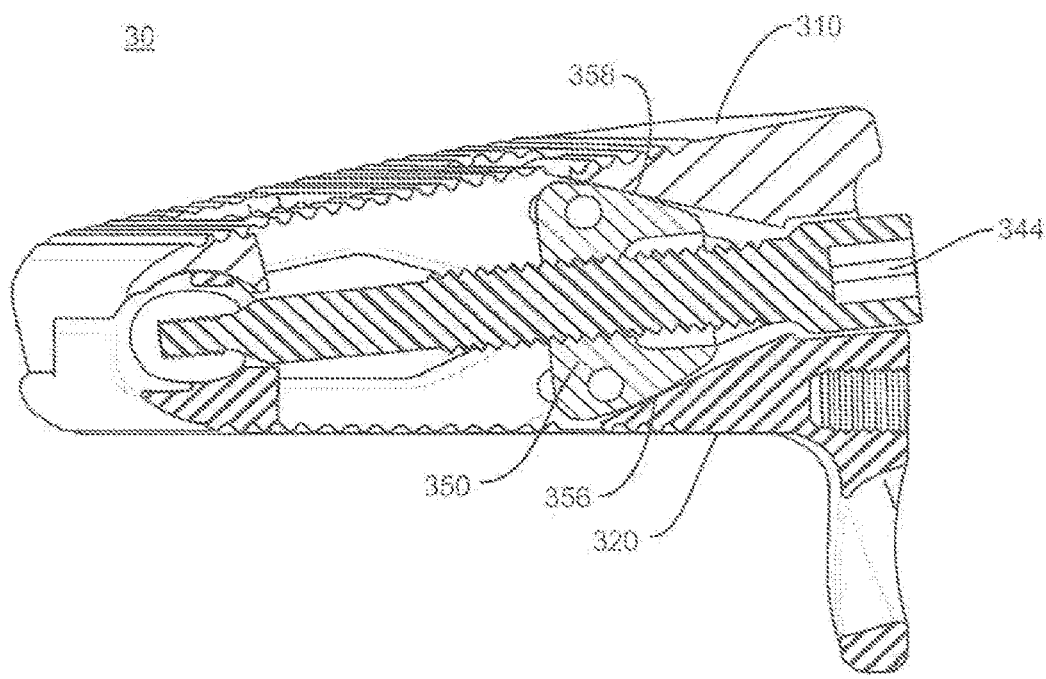
FIG. 29 is a cutaway side view of one embodiment of an expandable spinal implant in a closed configuration in accordance with the principles of the present disclosure.
Figure 30:
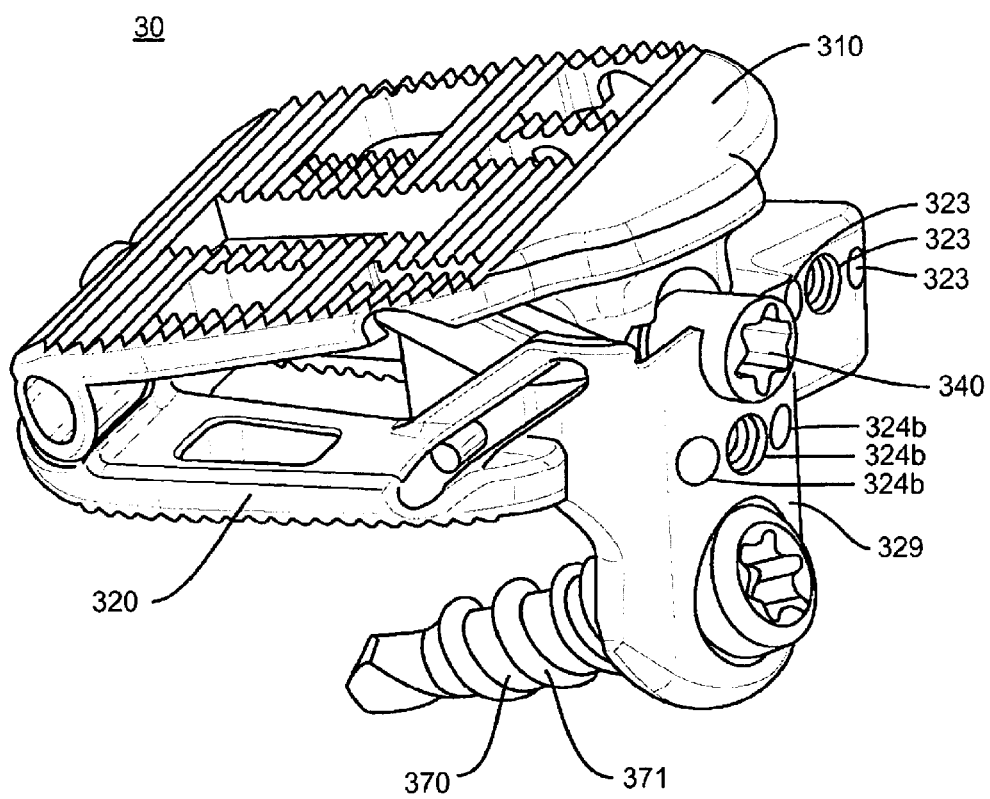
FIG. 30 is a perspective view of one embodiment of an expandable spinal implant in a partially expanded configuration in accordance with the principles of the present disclosure.
Figure 31A:
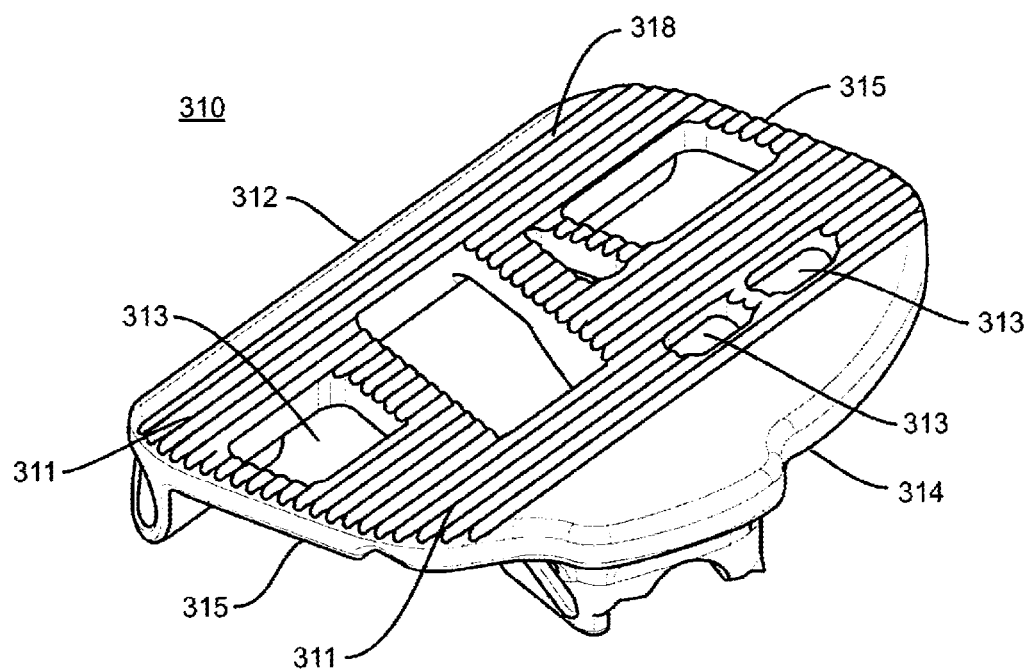
FIG. 31A is a perspective view and FIG. 31B is a plane view of the outer surface of one embodiment of an endplate in accordance with the principles of the present disclosure.
Figure 31B:
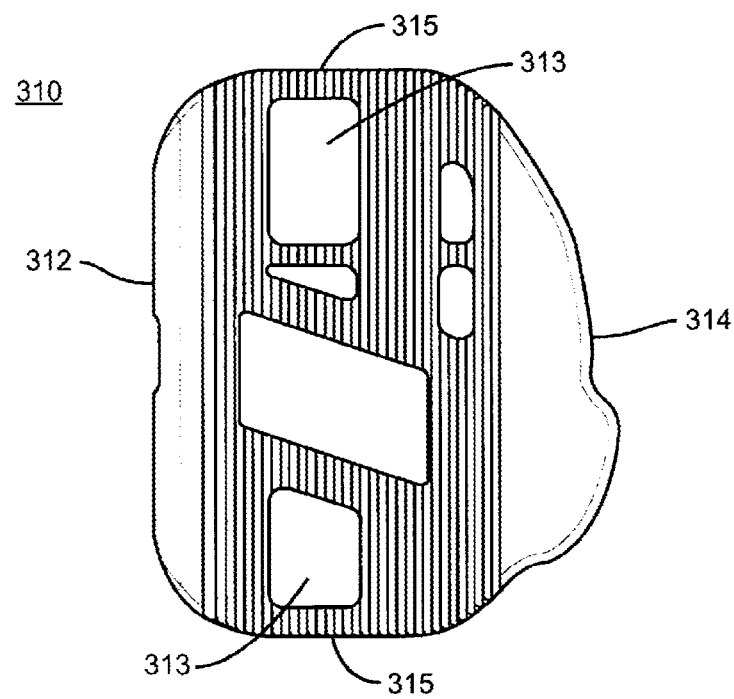

The expansion mechanism 240, 250 is designed to expand first endplate 210 and second endplate 220 away from each other as wedge 250 is translated towards second end 24 of implant 20 along rod assembly 240. Rod assembly 240 may be integrally formed, or may be formed of multiple components for, e.g., ease of manufacturing and/or assembly, like rod assembly 140 above. Rod assembly 240 may be secured to first and/or second endplates 210, 220 at a rod first end 245 such that a second rod end 246 may move relative to endplates 210, 220 as implant 20 is expanded or contracted (i.e., moved into an opened or closed configuration). In some embodiments, longitudinal axis E2-E2 of expansion mechanism 240, 250 may be aligned along mid-longitudinal axis L2-L2 of implant 20. In other embodiments, longitudinal axis E2-E2 of expansion mechanism 240, 250 may be offset from mid-longitudinal axis L2-L2 of implant 20, as depicted in FIG. 25, and/or may be angled obliquely to mid-longitudinal axis L2-L2, as depicted in FIG. 26. As described above for implant 10, second end 246 of rod assembly 240 may comprise an interface 244 configured to be operably engaged by a drive shaft (not shown) to rotate rod assembly 240. Rod interface 244 may comprise a drive receptacle configured to cooperate with an implant engaging end of the drive shaft. The drive connection between the drive shaft and rod interface 244 may comprise a variety of drive interfaces including but not limited to: multi-lobular drives; hexalobular drives; cross or Phillips head drives; straight or "flat head" drives; square or other polygonal drives; and/or combinations thereof. In other embodiments, first end 245 of rod assembly 240 may further comprise an interface configured to be operably engaged by a drive shaft to rotate rod assembly 240. In this way, implants of the present disclosure may be expanded from both an anterior/oblique and posterior approach, as depicted in FIGS. 25 and 26.

Figure 21A:
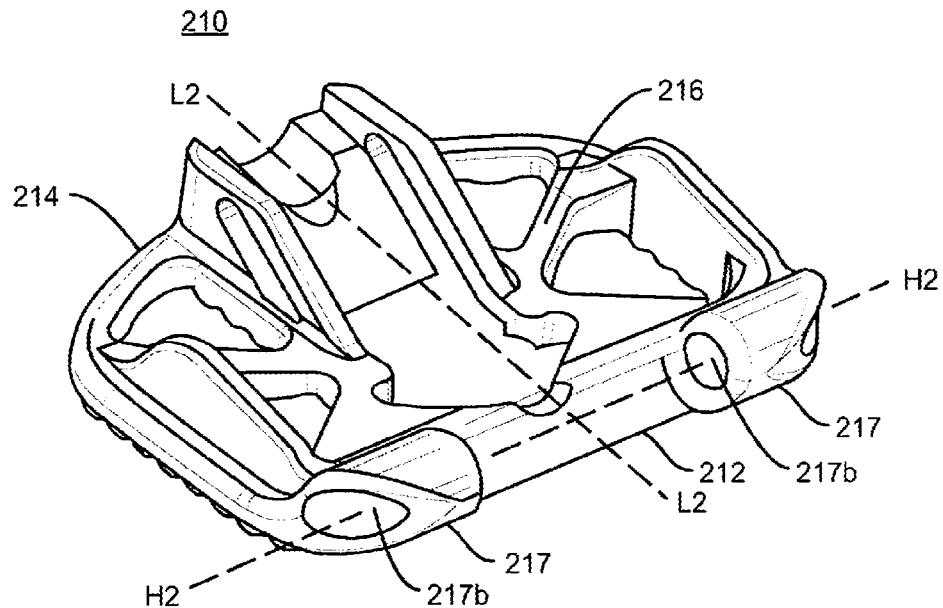
FIG. 21A is a perspective view and FIG. 21B is a plane view of the outer surface of one embodiment of an endplate in accordance with the principles of the present disclosure.
Figure 21B:
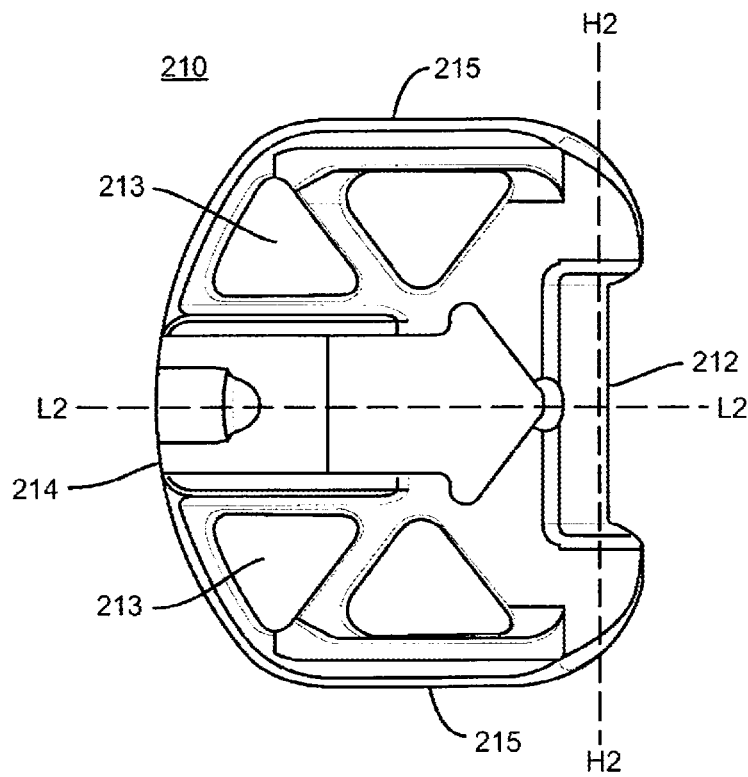
Figure 22A:
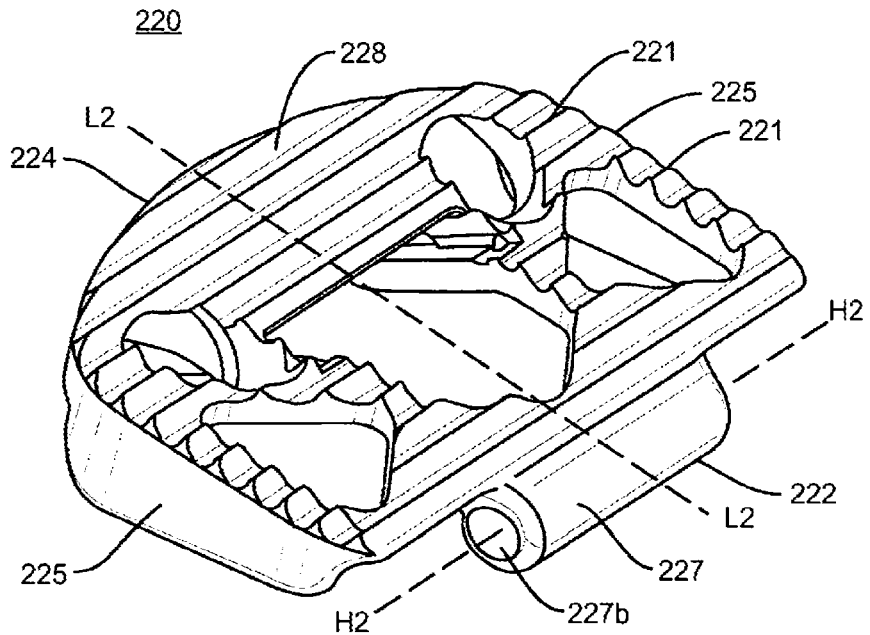
FIG. 22A is a perspective view and FIG. 22B is a plane view of the outer surface of one embodiment of an endplate in accordance with the principles of the present disclosure.
Figure 22B:
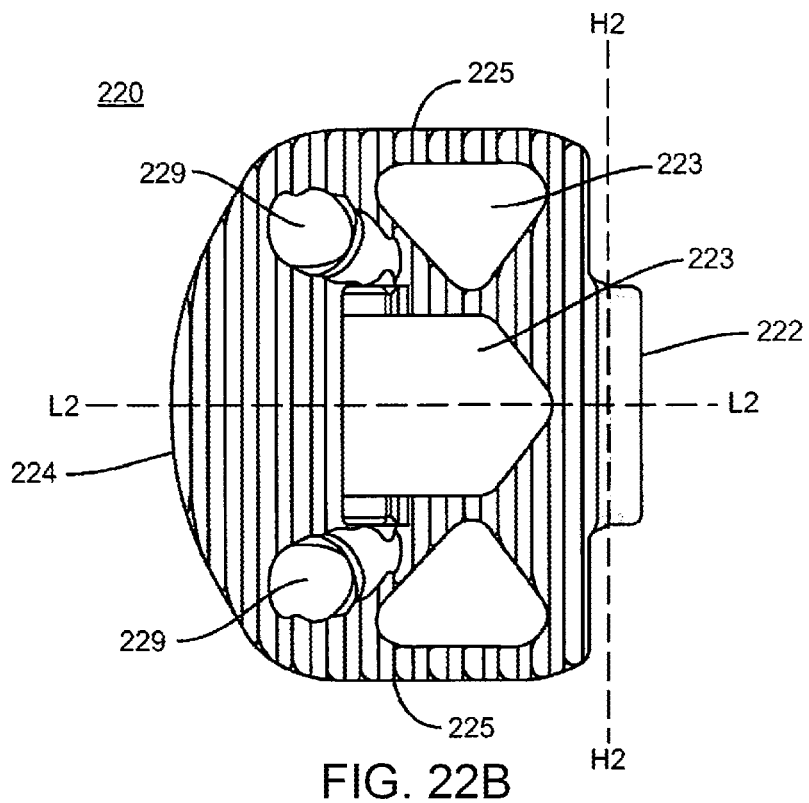
Figure 23A:
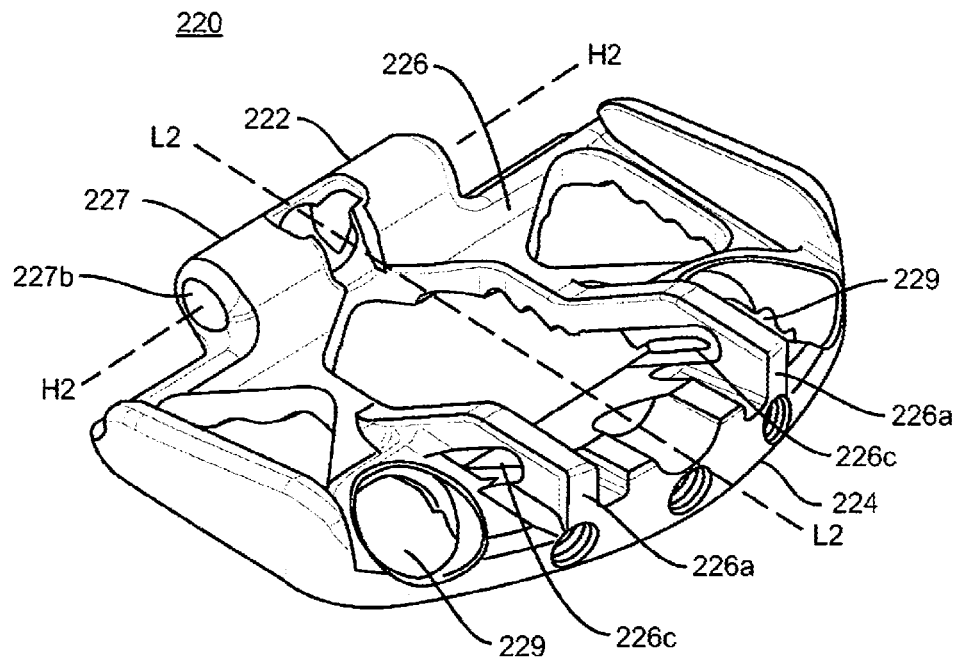
FIG. 23A is a perspective view and FIG. 23B is a plane view of the outer surface of one embodiment of an endplate in accordance with the principles of the present disclosure.
Figure 23B:
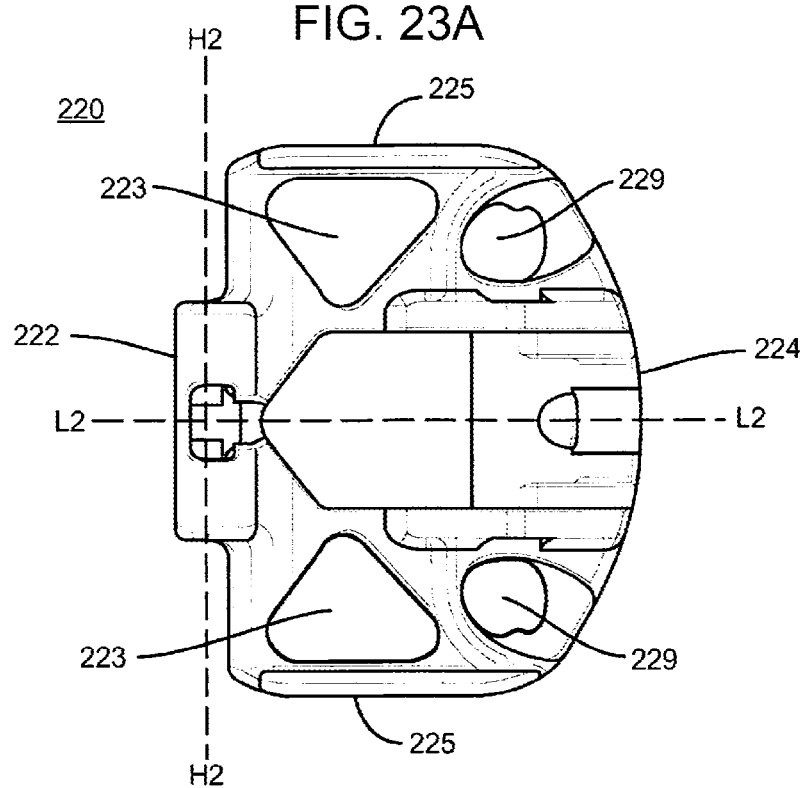

In some embodiments, upper surface 258 and lower surface 256 of wedge 250 may be ramped or wedge-shaped and suitable for urging a complementary ramped or contoured surface on the inside of endplates 210, 220 so as to gradually move endplates 210, 220 away from each other as wedge 250 is advanced along the rod assembly 240 towards second end 24 of implant 20. In some embodiments, various designs may be used to optimize the interaction of wedge 250 with endplates 210, 220. Such configurations may include, but are not limited to: sequential ramps or tapered surfaces with varying angles; shallow angle sequential ramps or tapered surfaces leading into higher angle sequential ramps or tapered surfaces, as well as other opening mechanisms (such as a lateral post and channel system). As shown in FIGS. 21 and 23, inner surfaces 216, 226 of endplates 210, 220 may comprise guidewalls 216a, 226a with lateral channels 216c, 226c disposed therein to engage lateral posts 255a extending from wedge 250. The mechanism provided by posts 255a and channels 216c, 226c may also aid in making the implant 20 expansion substantially reversible. For example, in the depicted embodiment, when wedge 250 is moved towards second end 24 of implant 20, posts 255a are moved in a first direction in channels 216c, 226c to expand first endplate 210 and second endplate 220 away from each other (which may result in implant 20 opening to the expanded configuration shown generally in FIG. 15), and when wedge 250 is moved towards first end 22 of implant 20, posts 255a are moved in a second direction in channels 216c, 226c to contract first endplate 210 and second endplate 220 towards each other (which may result in implant 20 returning to the closed or unexpanded configuration shown generally in FIG. 14). This reversible feature, combined with the threaded interaction between rod assembly 240 and wedge 250 renders implant 20 capable of being incrementally expanded or contracted through a substantially infinite adjustable range of motion (bounded only by the length of channels 216c, 226c). The design of the expansion mechanism, including the length and orientation of channels 216c, 226c, may be adjusted to determine the amount of lordotic expansion. In some embodiments, implant 20 provides 12 degrees of lordotic correction when in a collapsed/closed state and is capable of up to 32 degrees, 60 degrees, or more of lordotic or hyperlordotic expansion as wedge 250 is moved towards second end 24 of implant 20.

In the depicted embodiment, second endplate 220 may comprise apertures 229 through which one or more screws 270 may be disposed to secure endplate 220 within an intervertebral space. Screws 270 may comprise a threaded outer surface 271 that engages with the inner surface of aperture 229, which may also be threaded. The engagement between threaded outer surface 271 and inner surface of aperture 229 may be via pitch lock, major/minor lock, or any other thread/pitch interface.

Figure 24A:
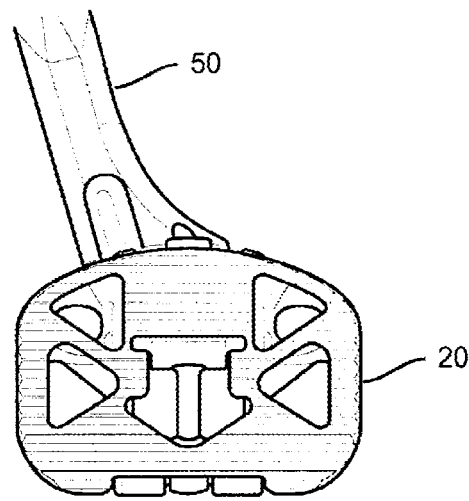
FIG. 24A depicts one embodiment of an expandable spinal implant and inserter in a first position in accordance with the principles of the present disclosure.
Figure 24B:
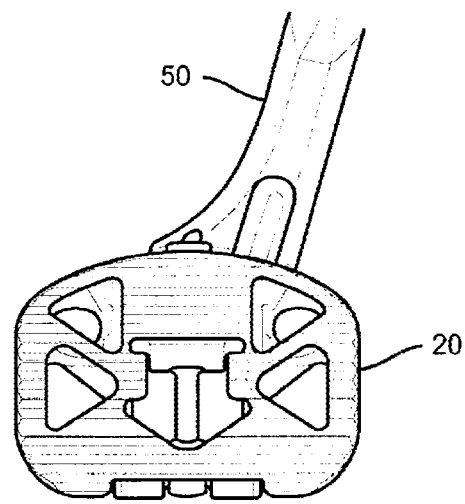
FIG. 24B depicts one embodiment of an expandable spinal implant and inserter in a second position in accordance with the principles of the present disclosure.
Figure 24C:
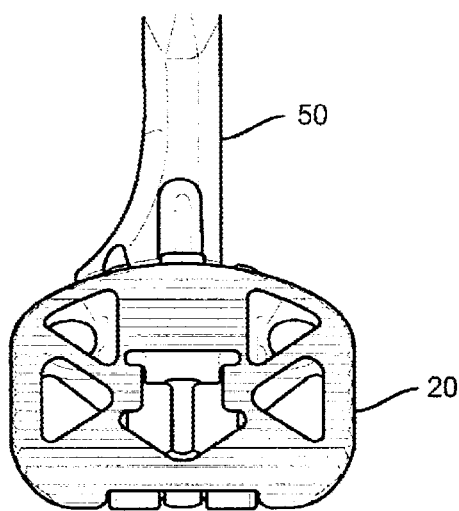
FIG. 24C depicts one embodiment of an expandable spinal implant and inserter in a third position in accordance with the principles of the present disclosure.

In some embodiments, second end 224 of second endplate 220 of implant 20 comprises inserter apertures 224b to engage with an insertion instrument 50 to form an expandable spinal implant system. As shown in FIGS. 24A-C, the number and arrangement of inserter apertures 224b allows the insertion instrument 50 to be attached to implant 20 in multiple orientations. This provides user flexibility to place implant 20 within intervertebral space with first endplate 210 superior to second endplate 220 or with first endplate 210 inferior to second endplate 220 such that screws 270 may be placed in either the cephalad or caudad vertebral bodies. In one embodiment, the inserter apertures are offset from mid-longitudinal axis which allows the inserter to be attached at a 15 degree angle allowing the device to be placed from an oblique approach.

FIGS. 27-36 show various configurations of an implant 30 embodiment according to the present disclosure. Implant 30 is generally similar in construction to implants 10, 20 described above and comprises a first endplate 310 and second endplate 320 operably engaged to one another via a hinge mechanism along the first end 32, and an expansion mechanism comprising a rod assembly 340 and a wedge 350 disposed between first and second endplates 310, 320. First endplate 310 includes a first end 312, a second end 314, opposing side surfaces 315 extending from the first end 312 of the first endplate to a portion of the second end 314 of the first endplate, and with the first endplate being therebetween, an inner surface 316, and an outer surface 318. Second endplate 320 includes a first end 322, a second end 324, opposing side surfaces 325 extending from the first end 322 of the second endplate to a portion of the second end 324 of the second endplate, and with the second endplate being therebetween, an inner surface 326, and an outer surface 328. In one embodiment, the endplates 310, 320 includes projections 311, 321 configured to engage a surface of the endplate of the adjacent vertebral body (not shown). Projections 311, 321 may comprise various anti-migration, anti-expulsion and/or osseointegration features including, but not limited to: ridges, teeth, pores, and coatings (including but not limited to porous titanium coatings such as those provided on Capstone PTC™ implants available from Medtronic). Endplates 310, 320 may further comprise at least one opening 313, 323 defined therein, configured to allow bone growth materials to be packed, placed, or loaded into implant 30.

The endplates 310, 320 may be operably engaged via a hinge mechanism located near or on the first ends 312 and 322. For example, first end 312 of first endplate 310 may comprise first and second hinge protrusions 317 extending along at least a portion of the length of first end 312 perpendicular to mid-longitudinal axis L3-L3. In some embodiments, first and second hinge protrusions are cylindrical and extend from lateral side surfaces 315 towards the mid-longitudinal axis L3-L3, and further comprise lumen 317b extending therethrough. First end 322 of second endplate 320 may also comprise a hinge protrusion 327. In some embodiments, hinge protrusion 327 is cylindrical and extends laterally along first end 322, and further comprises a lumen 327b extending therethrough. Lumens 317b, 327b of hinge protrusions 317, 327 may be co-axially aligned along a hinge axis H3-H3. A pin 330 may be disposed within lumens 217b, 327b of hinge protrusions 317, 327 to pivotably engage first endplate 310 to second endplate 320.

Figure 32A:
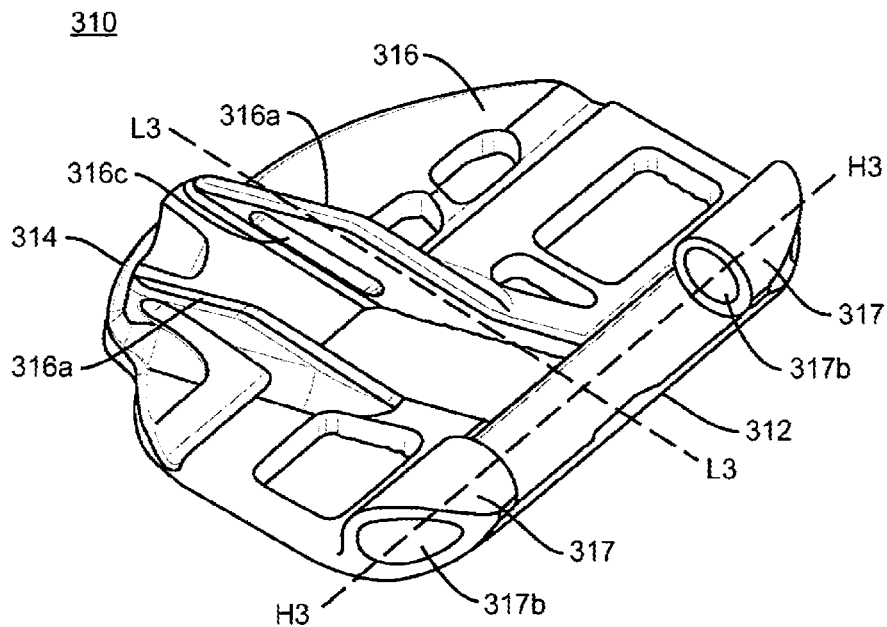
FIG. 32A is a perspective view and FIG. 32B is a plane view of the outer surface of one embodiment of an endplate in accordance with the principles of the present disclosure.
Figure 32B:
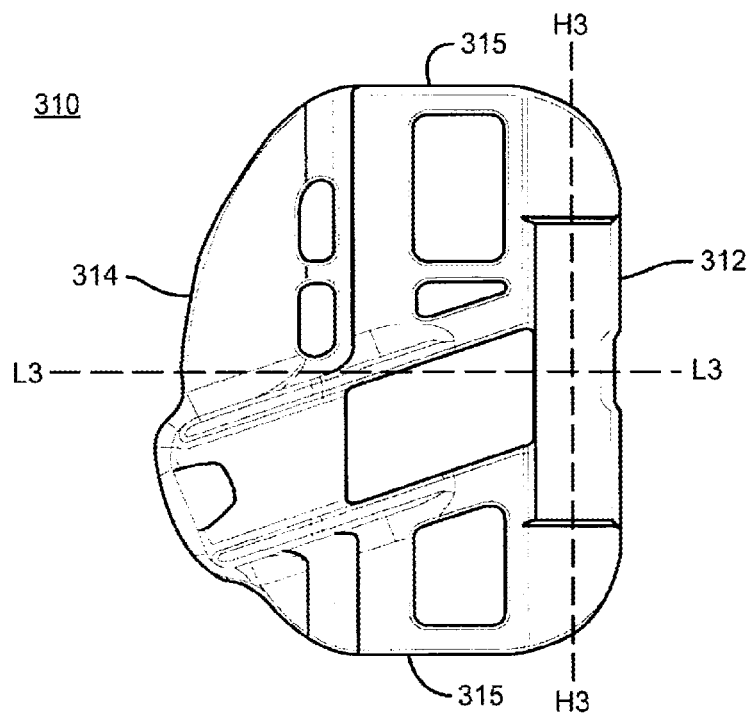
Figure 33A:
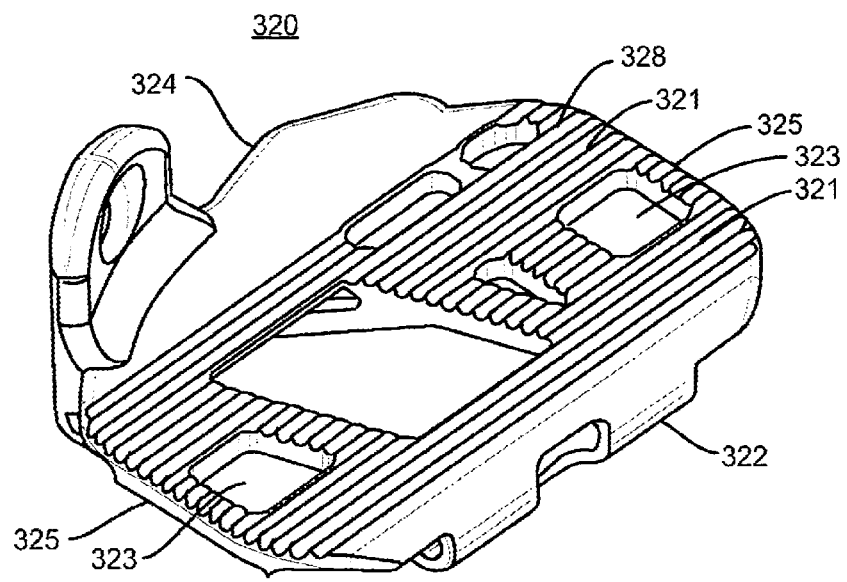
FIG. 33A is a perspective view and FIG. 33B is a plane view of the outer surface of one embodiment of an endplate in accordance with the principles of the present disclosure.
Figure 33B:
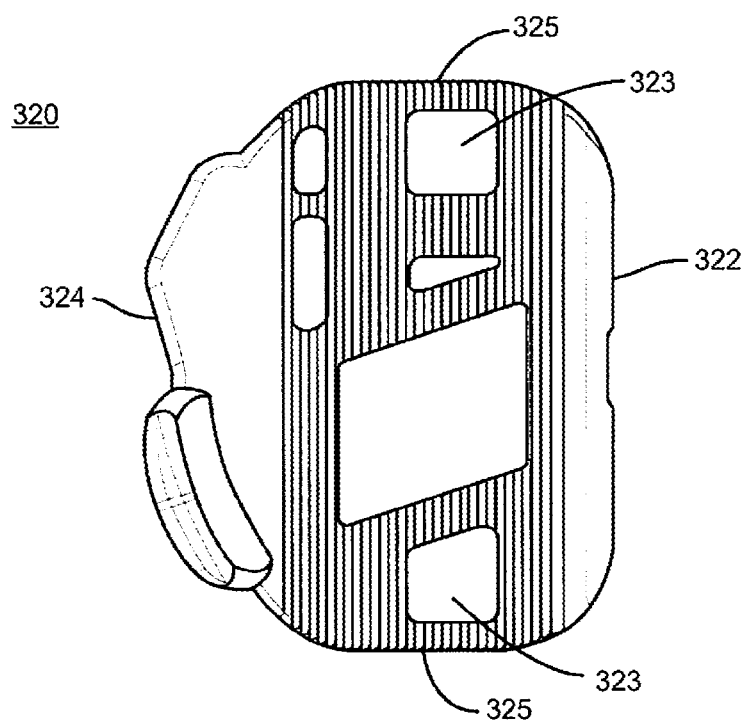
Figure 34A:
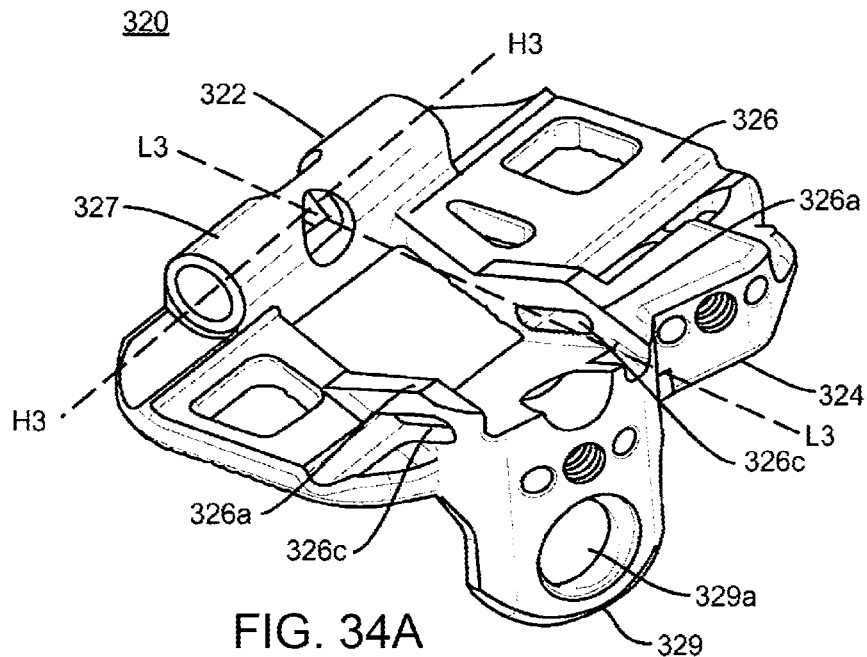
FIG. 34A is a perspective view and FIG. 34B is a plane view of the outer surface of one embodiment of an endplate in accordance with the principles of the present disclosure.
Figure 34B:
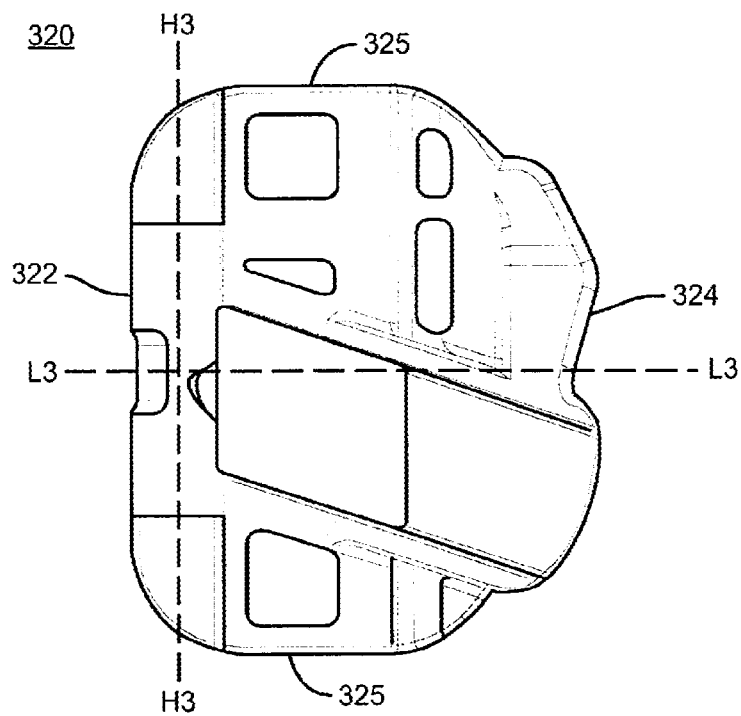
Figure 35:
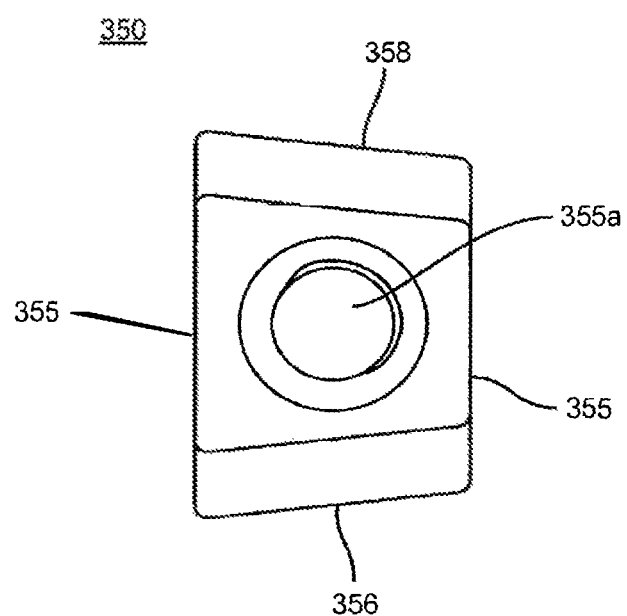
FIG. 35 is an end view of one embodiment of an expansion mechanism wedge in accordance with the principles of the present disclosure.
Figure 36:
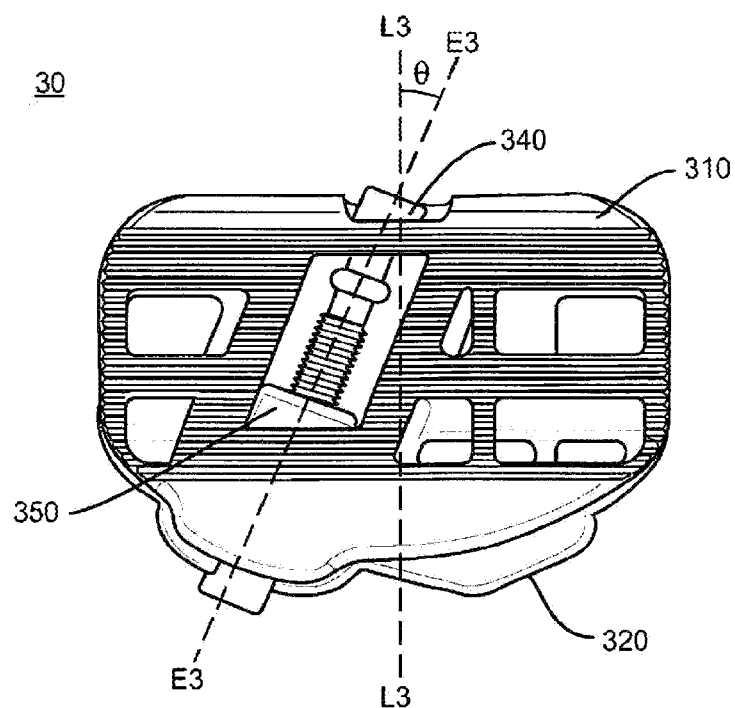
FIG. 36 is a top view of one embodiment of an endplate in accordance with the principles of the present disclosure.

The expansion mechanism 340, 350 is designed to expand first endplate 310 and second endplate 320 away from each other as wedge 350 is translated along rod assembly 340 towards second end 34 of implant 30. Rod assembly 340 may be integrally formed, or may be formed of multiple components for, e.g., ease of manufacturing and/or assembly, like rod assembly 140 above. Rod assembly 340 may be secured to first and/or second endplates 310, 320 at a first end 345 such that the second end 346 may move relative to endplates 310, 320 as implant 30 is expanded or contracted. In some embodiments, the longitudinal axis E3-E3 of expansion mechanism 340, 350 may be angled obliquely to mid-longitudinal axis L3-L3 at an angle θ, as depicted in FIG. 36. The shown device is angled at 15 degrees to optimize access for an oblique approach. As depicted in FIGS. 32, 34 and 35, first endplate 310, second endplate 320, and wedge 350 are designed with compound surface angles to ensure proper contact between wedge 350 and endplates 310, 320 throughout the range of translation As described above for implants 10, 20, the second end 346 of rod assembly 340 may comprise an interface 344 configured to be operably engaged by a drive shaft (not shown) to rotate the rod assembly 340. Rod interface 344 may comprise a drive receptacle configured to cooperate with an implant engaging end of the drive shaft. The drive connection between the drive shaft and rod interface 344 may comprise a variety of drive interfaces including but not limited to: multi-lobular drives; hexalobular drives; cross or Phillips head drives; straight or "flat head" drives; square or other polygonal drives; and/or combinations thereof. In other embodiments, first end 345 of rod assembly 340 may further comprise an interface configured to be operably engaged by a drive shaft to rotate rod assembly 340. In this way, implants of the present disclosure may be expanded from both an anterior/oblique and posterior approach, as depicted in FIG. 36.

In some embodiments, upper surface 358 and lower surface 356 of wedge 350 may be ramped or wedge-shaped and suitable for urging a complementary ramped or contoured surface on the inner surfaces 316, 326 of endplates 310, 320 so as to gradually move the endplates 310, 320 away from each other as wedge 350 is advanced along rod assembly 340. In some embodiments, various designs may be used to optimize the interaction of the wedge 350 with the endplates 210, 220. For example, as depicted in FIG. 35, one lateral side 355 of wedge 350 may be taller than opposing lateral side 355 of wedge 350 such that upper surface 358 and lower surface 356 may be angled. Inner surfaces 316, 326 of endplates 310, 320 are angled in a complementary manner in order to ensure proper contact between wedge 350 and endplates 310, 320 as wedge 350 is translated along rod assembly 340 at an angle oblique to mid-longitudinal axis L3-L3 of implant 30. Other configurations may include, but are not limited to: sequential ramps or tapered surfaces with varying angles; shallow angle sequential ramps or tapered surfaces leading into higher angle sequential ramps or tapered surfaces, as well as other opening mechanisms (such as a lateral post and channel system). In some embodiments, inner surfaces 316, 326 of endplates 310, 320 may comprise guidewalls 316a, 326a with lateral channels 316c, 326c disposed therein to engage lateral posts 355a extending from wedge 350. The mechanism provided by posts 355a and channels 316c, 326c may also aid in making the implant 30 expansion substantially reversible. For example, in the depicted embodiment, when wedge 350 is moved towards second end 34 of implant 30, posts 355a are moved in a first direction in channels 316c, 326c to expand first endplate 310 and second endplate 320 away from each other (which may result in implant 30 opening to the expanded configuration shown generally in FIG. 28), and when wedge 350 is moved towards second end 32 of implant 30, posts 355a are moved in a second direction in channels 316c, 326c to contract the first endplate 310 and second endplate 320 towards each other (which may result in the implant 30 returning to the closed or unexpanded configuration shown generally in FIG. 27). This reversible feature, combined with the threaded interaction between rod assembly 340 and wedge 350 renders implant 30 capable of being incrementally expanded or contracted through a substantially infinite adjustable range of motion (bounded only by the length of the channels 316c, 326c). The design of the expansion mechanism, including the length and orientation of the channels 316c, 326c, may be adjusted to determine the amount of lordotic expansion. In some embodiments, implant 30 provides 12 degrees of lordotic correction when in a collapsed/closed state and is capable of up to 30 degrees, 60 degrees, or more of lordotic or hyperlordotic expansion as the wedge 350 is moved towards second end 34 of implant 30.

In some embodiments, endplate 320 may comprise one or more tabs 329 comprising an aperture 329a through which one or more screws 370 may be disposed to secure endplate 320 within an intervertebral space. Screws 370 may comprise a threaded outer surface 371 that engages with the inner surface of aperture 329a, which may also be threaded. The engagement between threaded outer surface 371 and the inner surface of aperture 329a may be via pitch lock, major/minor lock, or any other thread/pitch interface.

In some embodiments, second end 324 of second endplate 320 of implant 30 comprises inserter apertures 324b to engage with an insertion instrument (not shown) to form an expandable spinal implant system. The number and arrangement of inserter apertures 324b allows the insertion instrument to be attached to implant 30 in multiple orientations. This provides user flexibility to place implant 30 within intervertebral space with first endplate 310 superior to second endplate 320 or with first endplate 310 inferior to second endplate 320 such that the tab 329 may be used to secure second endplate 320 in either the cephalad or caudad vertebral bodies.

Spinal implant systems of the present disclosure can be employed with a surgical arthrodesis procedure, such as, for example, an interbody fusion for treatment of an applicable condition or injury of an affected section of a spinal column and adjacent areas within a body, such as, for example, intervertebral disc space between adjacent vertebrae, and with additional surgical procedures and methods. In some embodiments, spinal implant systems can include an intervertebral implant that can be inserted with intervertebral disc space to space apart articular joint surfaces, provide support and maximize stabilization of vertebrae. In some embodiments, spinal implant systems may be employed with one or a plurality of vertebra.

Figure 37:
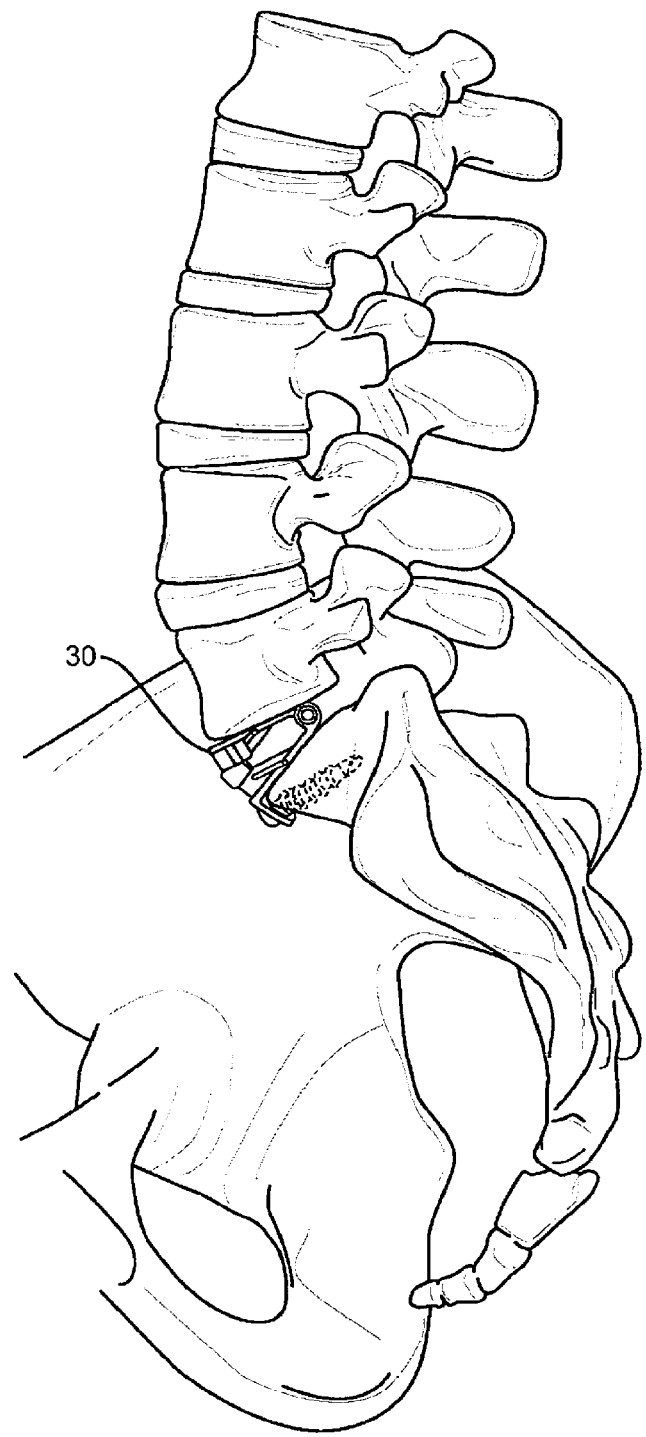
FIG. 37 is a side view of one embodiment of an expandable spinal implant as used in a spinal procedure in accordance with the principles of the present disclosure.
Figure 38:
FIG. 38 is a side view of one embodiment of an expandable spinal implant as used in a spinal procedure in accordance with the principles of the present disclosure.
Figure 39:
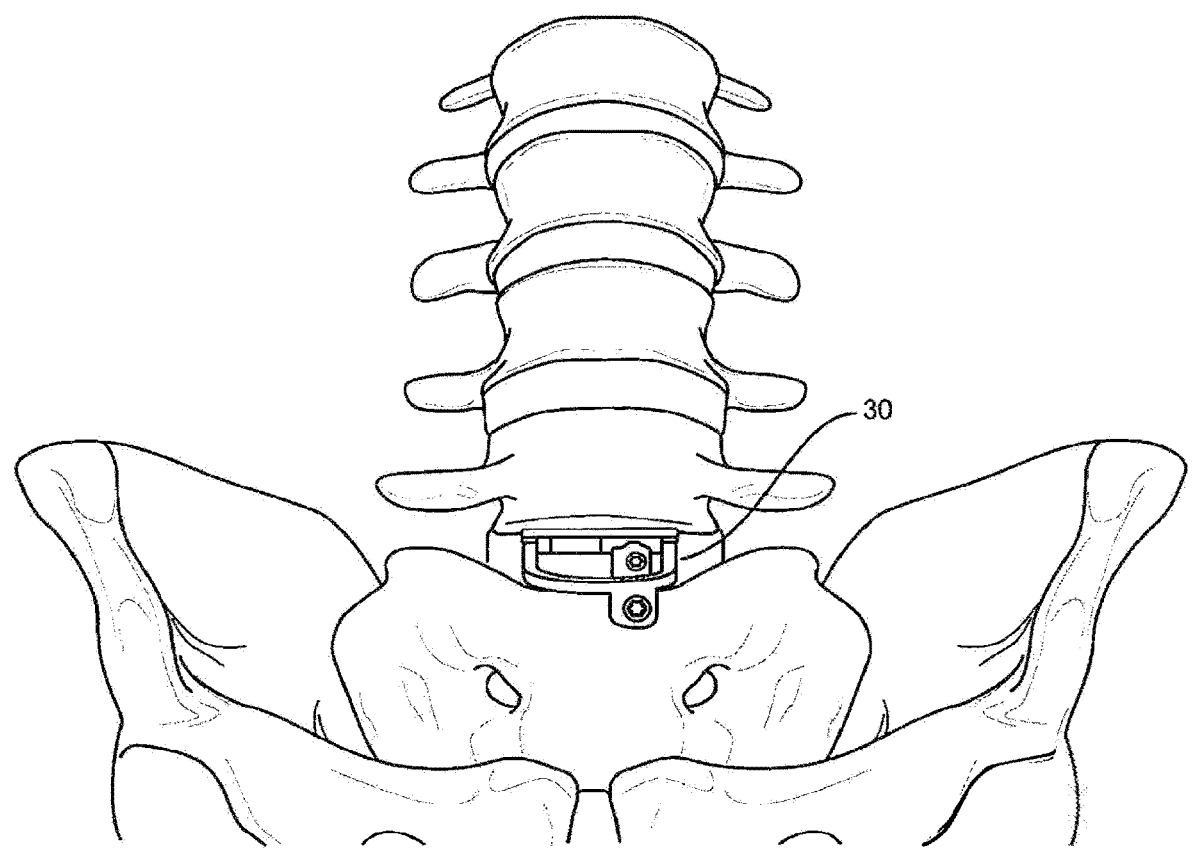
FIG. 39 is a side view of one embodiment of an expandable spinal implant as used in a spinal procedure in accordance with the principles of the present disclosure.

A medical practitioner obtains access to a surgical site including vertebrae such as through incision and retraction of tissues. Spinal implant systems of the present disclosure can be used in any existing surgical method or technique including open surgery, mini-open surgery, minimally invasive surgery and percutaneous surgical implantation, whereby vertebrae are accessed through a mini-incision, retractor, tube or sleeve that provides a protected passageway to the area, including, for example, an expandable retractor wherein the sleeve is formed from multiple portions that may be moved apart or together and may be inserted with the portions closed or together and then expanded to allow for insertion of implants of larger size than the closed cross section of the unexpanded retractor portions. In one embodiment, the components of the spinal implant system are delivered through a surgical pathway to the surgical site along a surgical approach into intervertebral disc space between vertebrae. Various surgical approaches and pathways may be used. For example, FIGS. 37-39 depict various views of a typical anterior lumbar interbody fusion (ALIF) approach using a spinal implant of the present disclosure. Unilateral approaches such as a transforaminal lumbar interbody fusion (TLIF) approach may also be used to place the implant in a substantially oblique position relative to the vertebrae. Multilateral approaches such as those disclosed in U.S. Pat. No. 9,730,684, incorporated herein by reference in its entirety, may also be used with spinal implant systems of the present disclosure.

As will be appreciated by one of skill in the art, a preparation instrument (not shown) may be employed to remove disc tissue, fluids, adjacent tissues and/or bone, and scrape and/or remove tissue from endplate surfaces of a first vertebra and/or endplate surface of a second vertebra in preparation for or as part of the procedures utilizing a system of the present disclosure. In some embodiments, the size of implant 10, 20, 30 is selected after trialing using trialing instruments (not shown) that may approximate the size and configuration of the implants 10, 20, 30. In some embodiments, such trials may be fixed in size and/or be fitted with expansion mechanisms similar to the various implant 10, 20, 30 embodiments described herein. In some embodiments, implant 10 may be visualized by fluoroscopy and oriented before introduction into intervertebral disc space. Furthermore, the insertion instruments 40, 50 and implants 10, 20, 30 may be fitted with fiducial markers to enable image guided surgical navigation to be used prior to and/or during a procedure.

Components of a spinal implant system of the present disclosure including implant 10, 20, 30 can be delivered or implanted as a pre-assembled device or can be assembled in situ. Components of spinal implant system including implant 10, 20, 30 may be expanded, contracted, completely or partially revised, removed or replaced in situ. In some embodiments, one or all of the components of spinal implant system 10, 20, 30 can be delivered to the surgical site via mechanical manipulation and/or a free hand technique.

In some embodiments, the spinal implant system includes an agent, including but not limited to the bone growth promoting materials described herein, which may be disposed, packed, coated or layered within, on or about the components and/or surfaces of the spinal implant system. In some embodiments the bone growth promoting materials may be pre-packed in the interior of the implant, and/or may be packed during or after implantation of the implant via a tube, cannula, syringe or a combination of these or other access instruments and may be further tamped into the implant before, during or after implantation. In some embodiments, the agent may include bone growth promoting material to enhance fixation of implants 10, 20, 30 with bony structures. In some embodiments, the agent may include one or a plurality of therapeutic agents and/or pharmacological agents for release, including sustained release, to treat, for example, pain, inflammation and degeneration.

In one embodiment, implants 10, 20, 30 may include fastening elements, which may include locking structure, configured for fixation with vertebrae to secure joint surfaces and provide complementary stabilization and immobilization to a vertebral region. In some embodiments, locking structure may include fastening elements, such as, for example, rods, plates, clips, hooks, adhesives and/or flanges. In some embodiments, the components of spinal implant system 20, 30 can be used with screws to enhance fixation. The components of the spinal implant system can be made of radiolucent materials such as polymers. Radiopaque markers may be included for identification under x-ray, fluoroscopy, CT or other imaging techniques. The insertion instruments 40, 50 may be radiolucent and may optionally include markers added at the tip and/or along the length of one or both of insertion instruments 40, 50 and the tube to permit them to be seen on fluoroscopy/x-ray while advancing into the patient. If the implants 10, 20, 30 includes radiolucent markers placed near the end this may permit visualization of the proximity of the tip of the tube moving toward the second ends 14, 24, 34 of implants 10, 20, 30.

In some embodiments, the use of microsurgical, minimally-invasive and image guided technologies may be employed to access, view and repair spinal deterioration or damage, with the aid of spinal implant system. Upon completion of the procedure, the non-implanted components, surgical instruments and assemblies of spinal implant system may be removed and the incision is closed. In some embodiments, the various instruments disclosed may be provided with fiducial markers or other elements suitable for use with surgical navigation systems (including, but not limited to the STEALTHSTATION® Navigation system available from Medtronic), such that a surgeon may view a projected trajectory or insertion pathway of the implants 10, 20, 30 relative to a patient's anatomy in real time and/or in near-real time.

It will be understood that the various independent components of the expandable spinal implants 10, 20, 30, and insertion instruments 40, 50 described herein may be combined in different ways according to various embodiments.

It will be understood that various modifications may be made to the embodiments disclosed herein. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A pivotably expandable spinal implant, comprising:
a first endplate including an outer surface configured to engage a first vertebra, the first endplate extending in a first longitudinal direction from a first proximal end to a first distal end;
a second endplate including an outer surface configured to engage a second vertebra, the second endplate extending in a second longitudinal direction from a second proximal end to a second distal end;
a pivotal joint that couples the first distal end of the first endplate to the second distal end of the second endplate;
a threaded rod extending in a third longitudinal direction from a proximal wall of the first endplate towards the pivotal joint, wherein the threaded rod is directly rotatably supported by a corresponding aperture extending through a proximally facing surface of the proximal wall of the first endplate, the proximal wall of the first endplate adjoining the first proximal end of the first endplate; and
a wedge disposed between the first endplate and the second endplate, the wedge including a threaded aperture;
wherein the threaded rod extends through the threaded aperture of the wedge such that rotation of the threaded rod causes the wedge to linearly translate along the threaded rod in the third longitudinal direction,
wherein, in a first mode of operation, translation of the wedge along the threaded rod in a first direction increases an angle of inclination between the first endplate outer surface and the second endplate outer surface,
wherein, in a second mode of operation, translation of the wedge along the threaded rod in a second direction, opposite the first direction, decreases the angle of inclination between the first endplate outer surface and the second endplate outer surface, and
wherein, an interior surface of the first endplate comprises at least one surface that directly contacts an upper surface of the wedge in the first mode of operation and the second mode of operation.

2. The pivotably expandable spinal implant of claim 1, wherein the upper surface of the wedge is inclined with respect to the outer surface of the second endplate.

3. The pivotably expandable spinal implant of claim 1, wherein the wedge comprises a pair of protrusions that are matingly engaged with corresponding channels formed on the interior surface of the first endplate.

4. The pivotably expandable spinal implant of claim 1, wherein the wedge comprises a pair of protrusions that are matingly engaged with corresponding channels formed on an interior surface of the second endplate.

5. The pivotably expandable spinal implant of claim 1, wherein an interior surface of the second endplate comprises at least one contact surface that directly engages a lower surface of the wedge in the first mode of operation.

6. The pivotably expandable spinal implant of claim 1, wherein the first direction is towards the first distal end and the second distal end.

7. The pivotably expandable spinal implant of claim 1, wherein the first distal end of the first endplate comprises a hinge protrusion extending in a lateral direction that is substantially perpendicular to the first longitudinal direction.

8. The pivotably expandable spinal implant of claim 7, wherein the second distal end of the second endplate comprises a relief area having a size and shape corresponding to the hinge protrusion.

9. The pivotably expandable spinal implant of claim 1, wherein the first endplate comprises at least one aperture configured to support a bone screw.

10. The pivotably expandable spinal implant of claim 1, wherein the upper surface of the wedge comprises a first chamfered end.

11. The pivotably expandable spinal implant of claim 1, wherein a lower surface of the wedge comprises a second chamfered end.

12. A pivotably expandable spinal implant, comprising:
a first endplate including an outer surface configured to engage a first vertebra, the first endplate extending in a first longitudinal direction from a first proximal end to a first distal end, the first distal end including a hinge protrusion extending in a lateral direction that is substantially perpendicular to the first longitudinal direction;
a second endplate including an outer surface configured to engage a second vertebra, the second endplate extending in a second longitudinal direction from a second proximal end to a second distal end, the second distal end including a relief area having a size and shape corresponding to the hinge protrusion;
a pivotal joint that couples the first distal end of the first endplate to the second distal end of the second endplate, the pivotal joint including the hinge protrusion of the first distal end and the relief area of the second distal end;
a threaded rod extending in a third longitudinal direction from a proximal face wall of the first endplate towards the pivotal joint; the threaded rod being directly rotatably supported by a corresponding aperture extending through a proximally facing surface of the proximal face wall of the first endplate, the proximal wall of the first endplate adjoining the first proximal end of the first endplate; and
a wedge disposed between the first endplate and the second endplate, the wedge including a threaded aperture;
wherein the threaded rod extends through the threaded aperture of the wedge such that rotation of the threaded rod causes the wedge to linearly translate along the threaded rod in the third longitudinal direction,
wherein, in a first mode of operation, translation of the wedge along the threaded rod in a first direction increases an angle of inclination between the first endplate outer surface and the second endplate outer surface,
wherein, in a second mode of operation, translation of the wedge along the threaded rod in a second direction, opposite the first direction, decreases the angle of inclination between the first endplate outer surface and the second endplate outer surface, and
wherein, an interior surface of the first endplate comprises at least one surface that directly contacts an upper surface of the wedge in the first mode of operation and the second mode of operation.

13. The pivotably expandable spinal implant of claim 12, wherein the wedge comprises a pair of protrusions that are matingly engaged with corresponding channels formed on the interior surface of the first endplate.

14. The pivotably expandable spinal implant of claim 13, wherein at least one of the first endplate and the second endplate comprises a bone screw aperture configured to support a bone screw.

* * * * *